(12) United States Patent
Cole et al.

(10) Patent No.: US 6,906,095 B2
(45) Date of Patent: Jun. 14, 2005

(54) INDOLYLALKYLIDENEHYDRAZINE-CARBOXIMIDAMIDE DERIVATIVES AS 5-HYDROXYTRYPTAMINE-6 LIGANDS

(75) Inventors: Derek Cecil Cole, New City, NY (US); Michael Gerard Kelly, Thousand Oaks, CA (US); David Scott Nunn, Valley Cottage, NY (US); Lynne Padilla Greenblatt, Lambertville, NJ (US)

(73) Assignee: Wyeth, Madison, NJ (US)

( * ) Notice: Subject to any disclaimer, the term of this patent is extended or adjusted under 35 U.S.C. 154(b) by 210 days.

(21) Appl. No.: 10/434,954

(22) Filed: May 9, 2003

(65) Prior Publication Data

US 2004/0002527 A1 Jan. 1, 2004

Related U.S. Application Data

(60) Provisional application No. 60/379,479, filed on May 10, 2002.

(51) Int. Cl.$^7$ ............... A61K 31/404; C07D 209/04
(52) U.S. Cl. ............... 514/415; 548/439; 548/491; 544/242; 544/335
(58) Field of Search ............... 548/439, 491; 544/242, 335; 514/415

(56) References Cited

U.S. PATENT DOCUMENTS 5,510,353 A * 4/1996 Giger et al. ............... 514/300

FOREIGN PATENT DOCUMENTS

EP 0505322 A1 9/1992
WO WO 94/14771 7/1994

OTHER PUBLICATIONS

Buchheit, Karl–Heinz et al., *Journal of Medicinal Chemistry, 1995*, 38:2326–2330.
Buchheit, Karl–Heinz et al., *Journal of Medicinal Chemistry, 1995*, 38:2331–2338.
Buchheit, Karl–Heinz et al., *Bioorganic & Medicinal Chemistry Letters, 1995*, 5(21):2495–2500.
Nguyen, Adrienne et al., *The Journal of Pharmacology and Experimental Therapeutics, 1997*, 280:1270–1276.
Husain, M.I. and Jamali, M.R., *Indian Journal of Chemistry, 1989*, 28B:532–534.

* cited by examiner

*Primary Examiner*—Golam M M Shameem
(74) *Attorney, Agent, or Firm*—Barbara L. Lences

(57) ABSTRACT

The present invention provides a compound of formula I and the use thereof for the therapeutic treatment of a disorder relating to or affected by the 5-HT6 receptor.

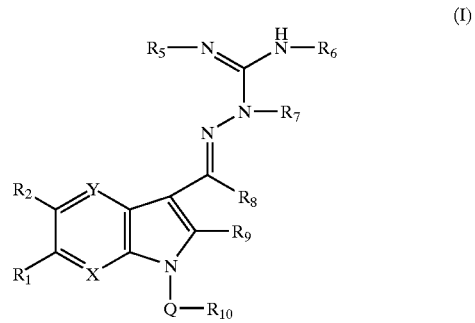

14 Claims, No Drawings

INDOLYLALKYLIDENEHYDRAZINE-CARBOXIMIDAMIDE DERIVATIVES AS 5-HYDROXYTRYPTAMINE-6 LIGANDS

This application claims priority from copending provisional application Ser. No. 60/379,479, filed May 10, 2002, the entire disclosure of which is hereby incorporated by reference.

BACKGROUND OF THE INVENTION

Various central nervous system disorders such as anxiety, depression, motor disorders, etc., are believed to involve a disturbance of the neurotransmitter 5-hydroxytryptamine (5-HT) or serotonin. Serotonin is localized in the central and peripheral nervous systems and is known to affect many types of conditions including psychiatric disorders, motor activity, feeding behavior, sexual activity, and neuroendocrine regulation among others. The effects of serotonin are regulated by the various 5-HT receptor subtypes. Known 5-HT receptors include the 5-HT1 family (e.g. 5-HT1A), the 5-HT2 family (e.g. 5-HT2A), 5-HT3, 5-HT4, 5-HT5, 5-HT6 and 5-HT7 subtypes.

The recently identified human 5-hydroxytryptamine-6 (5-HT6) receptor subtype has been cloned, and the extensive distribution of its mRNA has been reported. Highest levels of 5-HT6 receptor mRNA have been observed in the olfactory tubercle, the striatum, nucleus accumbens, dentate gyrus and CA1, CA2 and CA3 regions of the hippocampus. Lower levels of 5-HT6 receptor mRNA are seen in the granular layer of the cerebellum, several diencephalic nuclei, amygdala and in the cortex. Northern blots have revealed that 5-HT6 receptor mRNA appears to be exclusively present in the brain, with little evidence for its presence in peripheral tissues. The high affinity of a number of antipsychotic agents for the 5-HT6 receptor, in addition to its mRNA localization in striatum, olfactory tubercle and nucleus accumbens suggests that some of the clinical actions of these compounds may be mediated through this receptor. Therefore, 5-HT6 receptor ligands are believed to be of potential use in the treatment of certain CNS disorders such as anxiety, depression, epilepsy, obsessive compulsive disorder, attention deficit disorder, migraine, cognitive memory enhancement (e.g. for the treatment of Alzheimer's disease), sleep disorders, feeding disorders (e.g. anorexia or bulimia), neurodegenerative disorders (e.g. stroke or head trauma), panic attacks, withdrawal from drug abuse (e.g. cocaine, ethanol, nicotine or benzodiazepines), schizophrenia, or the like; or in the treatment of certain gastrointestinal disorders such as irritable bowel syndrome.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

These and other objects and features of the invention will become more apparent by the detailed description set forth hereinbelow.

SUMMARY OF THE INVENTION

The present invention provides an indolylalkylidenehydrazinecarboximidamide compound of formula I

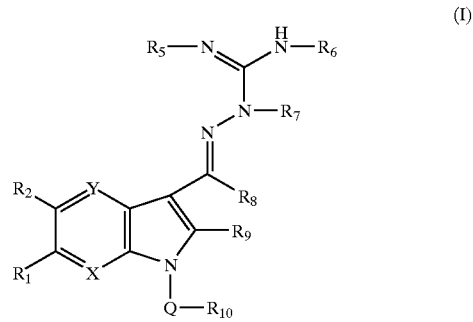

(I)

wherein
X is N or $CR_3$;
Y is N or $CR_4$;
Q is $SO_2$, CO, $CO_2$, $CONR_{11}$ or $CSNR_{12}$;
$R_1$, $R_2$, $R_3$ and $R_4$ are each independently H, halogen, CN, $OCO_2R_{13}$, $CO_2R_{14}$, $CONR_{15}R_{16}$, $NR_{17}SO_2R_{18}$, $NR_{19}COR_{28}$, $SO_nR_{20}$, $NR_{21}R_{22}$, $OR_{23}$, $COR_{24}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_5$, $R_6$ and $R_7$ are each independently H or a $C_1$–$C_6$alkyl, $C_2$–$C_6$alkenyl, $C_2$–$C_6$alkynyl, $C_3$–$C_{12}$cycloalkyl, cycloheteroalkyl, aryl or heteroaryl group each optionally substituted or $R_5$ and $R_6$ maybe taken together with the atoms to which they are attached to form an optionally substituted 5- to 7-membered ring;
$R_8$ is H or a $C_1$–$C_6$alkyl or $C_3$–$C_{10}$cycloalkyl group each optionally substituted;
$R_9$ is H, halogen, CN, $NO_2$, $NR_{25}R_{26}$, $OR_{27}$ or a $C_1$–$C_6$alkyl, aryl or heteroaryl group each optionally substituted or $R_8$ and $R_9$ may be taken together with the atoms to which they are attached to form an optionally substituted 5- to 7-membered ring optionally containing one or two heteroatoms selected from O, N or S;
$R_{10}$ is a $C_1$–$C_6$alkyl, aryl or heteroaryl group each optionally substituted or an optionally substituted 8- to 13-membered bicyclic or tricyclic ring system having a N atom at the bridgehead and optionally containing 1, 2 or 3 additional heteroatoms selected from N, O or S with the proviso that when $R_8$ is H or $C_1$–$C_6$alkyl and Q is CO then $R_{10}$ must be other than $C_1$–$C_6$alkyl or aryl;
n is 0 or an integer of 1 or 2;
$R_{11}$ and $R_{12}$ are each independently H or a $C_1$–$C_6$alkyl, aryl or heteroaryl group each optionally substituted;
$R_{13}$, $R_{14}$, $R_{18}$, $R_{20}$, $R_{23}$, $R_{24}$, $R_{27}$ and $R_{28}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_{15}$ and $R_{16}$ are each independently H or an optionally substituted $C_1$–$C_6$alkyl group; and
$R_{17}$, $R_{19}$, $R_{21}$, $R_{22}$, $R_{25}$ and $R_{26}$ are each independently H or an optionally substituted $C_1$–$C_4$alkyl group or $R_{21}$, and $R_{22}$ may be taken together with the atom to which they are attached to form a 5- to 7-membered ring optionally containing another heteroatom selected from O, N or S; or the stereoisomers thereof, the tautomers thereof or the pharmaceutically acceptable salts thereof.

The present invention also provides methods and compositions useful for the therapeutic treatment of central nervous system disorders related to or affected by the 5-HT6 receptor.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D. C. Rogers, Current Opinion in Investigational Drugs, 2001, 2(1):104–109, Pharma Press Ltd.

Surprisingly, it has now been found that indolylalkylidenehydralzinecarboximidamide derivatives of formula I demonstrate 5-HT6 affinity. Advantageously, said amide derivatives may be used as effective therapeutic agents for the treatment of central nervous system (CNS) disorders associated with or affected by the 5-HT6 receptor. Accordingly, the present invention provides indolylalkylidenehydrazinecarboximidamide derivatives of formula I.

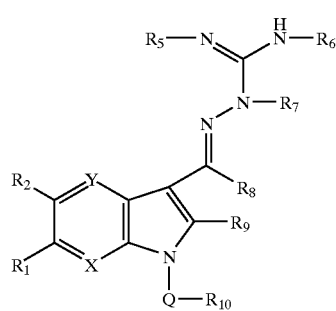

(I)

wherein

X is N or $CR_3$;

Y is N or $CR_4$;

Q is $SO_2$, CO, $CO_2$, $CONR_{11}$ or $CSNR_{12}$;

$R_1$, $R_2$, $R_3$ and $R_4$ are each independently H, halogen, CN, $OCO_2R_{13}$, $CO_2R_{14}$, $CONR_{15}R_{16}$, $NR_{17}SO_2R_{18}$, $NR_{19}COR_{28}$, $SO_nR_{20}$, $NR_{21}R_{22}$, $OR_{23}$, $COR_{24}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_5$, $R_6$ and $R_7$ are each independently H or a $C_1$–$C_6$alkyl, $C_2$–$C_6$alkenyl, $C_2$–$C_6$alkynyl, $C_3$–$C_{12}$Cycloalkyl, cycloheteroalkyl, aryl or heteroaryl group each optionally substituted or $R_5$ and $R_6$ maybe taken together with the atoms to which they are attached to form an optionally substituted 5- to 7-membered ring;

$R_8$ is H or a $C_1$–$C_6$alkyl or $C_3$–$C_{10}$cycloalkyl group each optionally substituted; $R_9$ is H, halogen, CN, $NO_2$, $NR_{25}R_{26}$, $OR_{27}$ or a $C_1$–$C_6$alkyl, aryl or heteroaryl group each optionally substituted or $R_8$ and $R_9$ may be taken together with the atoms to which they are attached to form an optionally substituted 5- to 7-membered ring optionally containing one or two heteroatoms selected from O, N or S;

$R_{10}$ is a $C_1$–$C_6$alkyl, aryl or heteroaryl group each optionally substituted or an optionally substituted 8- to 13-membered bicyclic or tricyclic ring system having a N atom at the bridgehead and optionally containing 1, 2 or 3 additional heteroatoms selected from N, O or S with the proviso that when $R_8$ is H or $C_1$–$C_6$alkyl and Q is CO then $R_{10}$,must be other than $C_1$–$C_6$alkyl or aryl;

n is 0 or an integer of 1 or 2;

$R_{11}$ and $R_{12}$ are each independently H or a $C_1$–$C_6$alkyl, aryl or heteroaryl group each optionally substituted;

$R_{13}$, $R_{14}$, $R_{18}$, $R_{20}$, $R_{23}$, $R_{24}$, $R_{27}$ and $R_{28}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{15}$ and $R_{16}$ are each independently H or an optionally substituted $C_1$–$C_6$alkyl group; and $R_{17}$, $R_{19}$, $R_{21}$, $R_{22}$, $R_{25}$ and $R_{26}$ are each independently H or an optionally substituted $C_1$–$C_4$alkyl group or $R_{21}$, and $R_{22}$ may be taken together with the atom to which they are attached to form a 5- to 7-membered ring optionally containing another heteroatom selected from O, N or S; or the stereoisomers thereof, the tautomers thereof or the pharmaceutically acceptable salts thereof.

As used in the specification and claims, the term halogen designates Br, Cl, I or F and the term cycloheteroalkyl designates a $C_5$–$C_7$cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein W is NR, O or S; and R is H or an optional substituent as described hereinbelow:

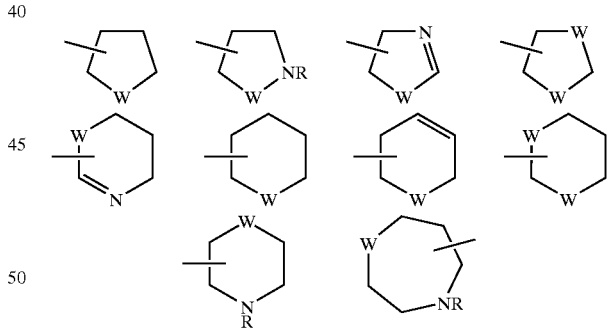

Similarly, as used in the specification and claims, the term heteroaryl designates a $C_5$–$C_{10}$ aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolinyl, benzothienyl, benzofuranyl, benzisoxazolyl or the like. The term aryl designates carbocyclic aromatic ring systems such as phenyl, naphthyl, or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

Exemplary of the 8- to 13-membered bicyclic or tricyclic ring systems having a N atom at the bridgehead and optionally containing 1, 2 or 3 additional heteroatoms selected from N, O or S included in the term as designated herein are the following ring systems wherein $W_2$ is NR, O or S; and R is H or an optional substituent as described hereinbelow:

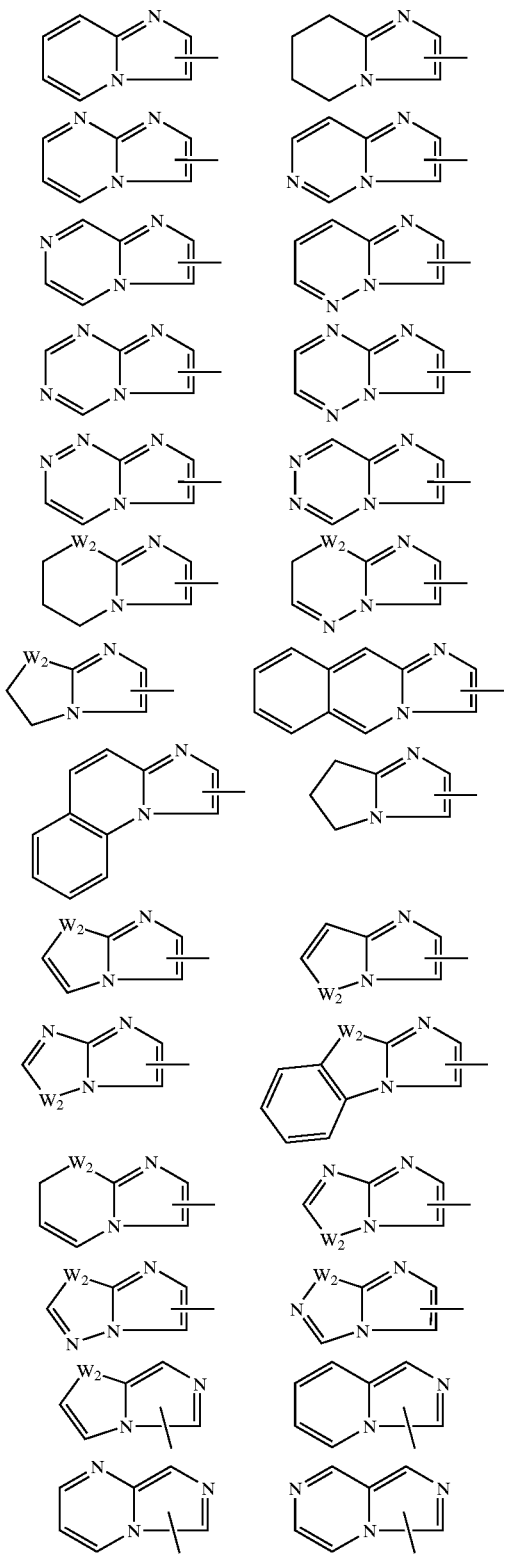

-continued

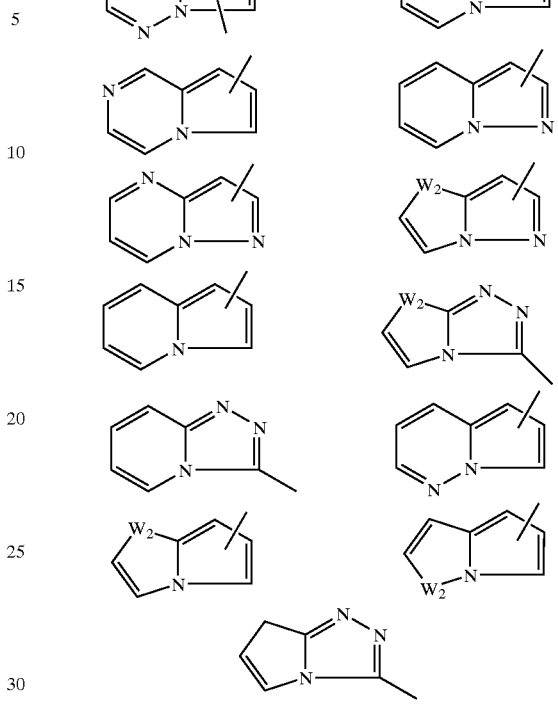

In the specification and claims, when the terms $C_1-C_6$ alkyl, $C_2-C_6$ alkenyl, $C_2-C_6$ alkynyl, $C_3-C_7$ cycloalkyl, cycloheteroalkyl, aryl, heteroaryl or 8- to 13-membered bicyclic or tricyclic ring system having a N atom at the bridgehead are designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulfinyl, alkylsulfonyl, carbamoyl, alkylamido, phenyl, phenoxy, benzyl, benzyloxy, cycloheteroalkyl or cycloalkyl groups, preferably halogen atoms or lower alkyl groups. Typically, 0–3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of formula I, the stereoisomers thereof, the tautomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of formula I wherein Q is $SO_2$. Also preferred are those compounds of formula I wherein $R_{10}$ is an aryl or heteroaryl group each optionally substituted or an optionally substituted 8- to 13-member bicyclic or tricyclic ring system having a N atom at the bridgehead and optionally containing 1, 2 or 3 additional heteroatoms selected from N, O or S. Another group of preferred compounds of formula I are those compounds wherein X is $CR_3$ and Y is $CR_4$.

More preferred compounds of the invention are those compounds of formula I wherein Q is $SO_2$ and $R_9$ is H. Another group of more preferred compounds are those compounds of formula I wherein Q is $SO_2$; X is $CR_3$; Y is $CR_4$; and $R_9$ is H. Further more preferred compounds are those formula I compounds wherein Q is $SO_2$; X is $CR_3$; Y is $CR_4$; $R_9$ is H; and $R_{10}$ is an aryl or heteroaryl group each optionally substituted or an optionally substituted 8- to 15-member bicyclic or tricyclic ring system having a N atom at the bridgehead optionally containing 1, 2 or 3 additional heteroatoms selected from N, O or S.

Exemplary of the compounds of the invention are:
1-[(4-methylphenyl)sulfonyl]-1H-indole-3-carbaldehyde 1,4,5,6-tetrahydropyrimidin-2-ylhydrazone,
2-({1-[(4-methylphenyl)sulfonyl]-1H-indol-3-l}methylidene)hydrazinecarboximidamide,
1-[(4-methylphenyl)sulfonyl]-1H-indole-3-carbaldehyde 4,5-dihydro-1H-imidazol-2-yl(methyl)hydrazone,
2-{cyclohexyl[1-(phenylsulfonyl)-1H-indol-3-yl]methylidene}hydrazinecarboximidamide,
2-{2-methyl-1-[1-(phenylsulfonyl)-1H-indol-3-yl]propylidene}hydrazinecarboximidamide,
2-{2-phenyl-1-[1-(phenylsulfonyl)-1H-indol-3-yl]ethylidene}hydrazinecarboximidamide,
2-{3-methyl-1-[1-(phenylsulfonyl)-1H-indol-3-yl]butylidene}hydrazinecarboximidamide,
2-{(E,2E)-3-(2-chlorophenyl)-1-[1-(phenylsulfonyl)-1H-indol-3-yl]prop-2-enylidene}-hydrazinecarboximidamide,
2-{1-[1-(phenylsulfonyl)-1H-indol-3-yl]ethylidene}hydrazinecarboximidamide,
2-{1-[5-chloro-2-methyl-1-(phenylsulfonyl)-1H-indol-3-yl]ethylidene}hydrazinecarboximidamide
2-{1-[2-(4-fluorophenyl)-1-(phenylsulfonyl)-1H-indol-3-yl]ethylidene}hydrazinecarboximidamide
2-{1-[2-(3-chloro-4-fluorophenyl)-1-(phenylsulfonyl)-1H-indol-3-yl]ethylidene}hydrazinecarboximidamide,
2-{1-[2-(3,4-difluorophenyl)-1-(phenylsulfonyl)-1H-indol-3-yl]ethylidene}hydrazinecarboximidamide,
2-{1-[2-(2-naphthyl)-1-(phenylsulfonyl)-1H-indol-3-yl]ethylidene}hydrazinecarboximidamide,
2-{1-[2-phenyl-1-(phenylsulfonyl)-1H-indol-3-yl]ethylidene}hydrazinecarboximidamide,
2-{1-[5-cyano-1-(phenylsulfonyl)-1H-indol-3-yl]ethylidene}hydrazinecarboximidamide,
2-{1-[5-iodo-1-(phenylsulfonyl)-1H-indol-3-yl]ethylidene}hydrazinecarboximidamide,
2-{1-[5-nitro-1-(phenylsulfonyl)-1H-indol-3-yl]ethylidene}hydrazinecarboximidamide,
2-{1-[5-fluoro-1-(phenylsulfonyl)-1H-indol-3-yl]ethylidene}hydrazinecarboximidamide,
2-{[5-methoxy-1-(phenylsulfonyl)-1H-indol-3-yl]methylidene}hydrazinecarboximidamide,
2-{[5-(benzyloxy)-1-(phenylsulfonyl)-1H-indol-3-yl]methylidene}hydrazinecarboximidamide,
2-(1-{1-[(2-amino-4-methyl-1,3-thiazol-5-yl)sulfonyl]-1H-indol-3-yl}ethylidene)hydrazinecarboximidamide,
2-(1-{1-[(4-aminophenyl)sulfonyl]-1H-indol-3-yl}ethylidene)hydrazinecarboximidamide,
2-{1-[1-(2,1,3-benzothiadiazol-4-ylsulfonyl)-1H-indol-3-yl]ethylidene}hydrazinecarboximidamide,
2-{1-[1-([1,1'-biphenyl]-4-ylsulfonyl)-1H-indol-3-yl]ethylidene}hydrazinecarboximidamide,
2-(1-{1-[(4-bromo-2,5-dichlorothien-3-yl)sulfonyl]-1H-indol-3-yl}ethylidene)hydrazinecarboximidamide,
2-(1-{1-[(4-bromo-5-chlorothien-2-yl)sulfonyl]-1H-indol-3-yl}ethylidene)hydrazinecarboximidamide,
2-(1-{1-[(3-bromo-5-chlorothien-2-yl)sulfonyl]-1H-indol-3-yl}ethylidene)hydrazinecarboximidamide,
2-(1-{1-[(4-bromophenyl)sulfonyl]-1H-indol-3-yl}ethylidene)hydrazinecarboximidamide,
2-(1-{1-[(2-bromophenyl)sulfonyl]-1H-indol-3-yl}ethylidene)hydrazinecarboximidamide,
2-(1-{1-[(3-bromophenyl)sulfonyl]-1H-indol-3-yl}ethylidene)hydrazinecarboximidamide,
2-(1-{1-[(5-bromothien-2-yl)sulfonyl]-1H-indol-3-yl}ethylidene)hydrazinecarboximidamide,
2-(1-{1-[(5-chloro-2-methoxyphenyl)sulfonyl]-1H-indol-3-yl}ethylidene)hydrazinecarboximidamide,
2-(1-{1-[(5-chloro-3-methyl-1-benzothien-2-yl)sulfonyl]-1H-indol-3-yl}ethylidene)hydrazinecarboximidamide,
2-(1-{1-[(6-chloroimidazo[2,1-b][1,3]thiazol-5-yl)sulfonyl]-1H-indol-3-yl}ethylidene)hydrazinecarboximidamide,
2-(1-{1-[(5-chlorothien-2-yl)sulfonyl]-1H-indol-3-yl}ethylidene)hydrazinecarboximidamide,
2-[1-(1-{[5-(dimethylamino)-1-naphthyl]sulfonyl}-1H-indol-3-yl)ethylidene]hydrazinecarboximidamide,
2-(1-{1-[(4,5-dibromothien-2-yl)sulfonyl]-1H-indol-3-yl}ethylidene)hydrazinecarboximidamide,
2-(1-{1-[(2,5-dichlorophenyl)sulfonyl]-1H-indol-3-yl}ethylidene)hydrazinecarboximidamide,
2-(1-{1-[(2,5-dichlorothien-3-yl)sulfonyl]-1H-indol-3-yl}ethylidene)hydrazinecarboximidamide,
2-(1-{1-[(4,5-dichlorothien-2-yl)sulfonyl]-1H-indol-3-yl}ethylidene)hydrazinecarboximidamide,
2-(1-{1-[(3,5-dimethylisoxazol-4-yl)sulfonyl]-1H-indol-3-yl}ethylidene)hydrazinecarboximidamide,
2-(1-{1-[(4-fluorophenyl)sulfonyl]-1H-indol-3-yl}ethylidene)hydrazinecarboximidamide,
2-{1-[1-({5-[1-methyl-5-(trifluoromethyl)-1H-pyrazol-3-yl]thien-2-yl}sulfony)-1H-indol-3-yl]ethylidene}hydrazinecarboximidamide,
2-(1-{1-[(2-methyl-5-nitrophenyl)sulfonyl]-1H-indol-3-yl}ethylidene)hydrazinecarboximidamide,
2-(1-{1-[(1-methyl-1H-imidazol-4-yl)sulfonyl]-1H-indol-3-yl}ethylidene)hydrazinecarboximidamide,
2-[1-(1-{[4-(methylsulfonyl)phenyl]sulfonyl}-1H-indol-3-yl)ethylidene]hydrazinecarboximidamide,
2-{1-[1-({5-[2-(methylthio)pyrimidin-4-yl]thien-2-yl}sulfonyl)-1H-indol-3-yl]ethylidene}-hydrazinecarboximidamide,
2-{1-[1-(1-naphthylsulfonyl)-1H-indol-3-yl]ethylidene}hydrazinecarboximidamide,
2-(1-{1-[(2-nitrophenyl)sulfonyl]-1H-indol-3-yl}ethylidene)hydrazinecarboximidamide, 2-(1-{1-[(4-nitrophenyl)sulfonyl]-1H-indol-3-yl}ethylidene)hydrazinecarboximidamide,
2-(1-{1-[(5-pyridin-2-ylthien-2-yl)sulfonyl]-1H-indol-3-yl}ethylidene)hydrazinecarboximidamide,
2-[1-(1-{[4-(trifluoromethoxy)phenyl]sulfonyl}-1H-indol-3-yl)ethylidene]hydrazinecarboximidamide,
phenyl 3-(1-{2-[amino(imino)methyl]hydrazono}ethyl)-1H-indole-1-carboxylate,
3-(1-{2-[amino(imino)methyl]hydrazono}ethyl)-N-phenyl-1H-indole-1-carboxamide,
2-[1-(1-benzoyl-1H-indol-3-yl)ethylidene]hydrazinecarboximidamide,
2-{1-[1-(methylsulfonyl)-1H-indol-3-yl]ethylidene}hydrazinecarboximidamide,
2-{1-[1-(methylsulfonyl)-1H-indol-3-yl]pentylidene}hydrazinecarboximidamide,
2-{cyclopropyl[1-(methylsulfonyl)-1H-indol-3-yl]methylidene}hydrazinecarboximidamide,
2-{1-[1-(butylsulfonyl)-1H-indol-3-yl]ethylidene}hydrazinecarboximidamide,
2-{1-[1-(butylsulfonyl)-1H-indol-3-yl]pentylidene}hydrazinecarboximidamide,
2-[[1-(butylsulfonyl)-1H-indol-3-yl](cyclopropyl)methylidene]hydrazinecarboximidamide,
2-(1-{1-[(4-methoxyphenyl)sulfonyl]-1H-indol-3-yl}ethylidene)hydrazinecarboximidamide,
2-(1-{1-[(4-methoxyphenyl)sulfonyl]-1H-indol-3-yl}pentylidene)hydrazinecarboximidamide,
2-(cyclopropyl{1-[(4-methoxyphenyl)sulfonyl]-1H-indol-3-yl}methylidene)hydrazinecarboximidamide,
2-{1-[1-(2-naphthylsulfonyl)-1H-indol-3-yl]ethylidene}hydrazinecarboximidamide,
2-{1-[1-(2-naphthylsulfonyl)-1H-indol-3-yl]pentylidene}hydrazinecarboximidamide,
2-{cyclopropyl[1-(2-naphthylsulfonyl)-1H-indol-3-yl]methylidene}hydrazinecarboximidamide,
2-{1-[1-(phenylsulfonyl)-1H-indol-3-yl]pentylidene}hydrazinecarboximidamide,
2-{cyclopropyl[1-(phenylsulfonyl)-1H-indol-3-yl]methylidene}hydrazinecarboximidamide,
2-(1-{1-[(3,4-dimethoxyphenyl)sulfonyl]-1H-indol-3-yl}ethylidene)hydrazinecarboximidamide,
2-(1-{1-[(3,4-dimethoxyphenyl)sulfonyl]-1H-indol-3-yl}pentylidene)hydrazinecarboximidamide,
2-(cyclopropyl{1-[(3,4-dimethoxyphenyl)sulfonyl]-1H-indol-3-yl}methylidene)hydrazinecarboximidamide,
2-{1-[5-chloro-1-(methylsulfonyl)-1H-indol-3-yl]ethylidene}hydrazinecarboximidamide,
2-{1-[5-chloro-1-(methylsulfonyl)-1H-indol-3-yl]pentylidene}hydrazinecarboximidamide,
2-[[5-chloro-1-(methylsulfonyl)-1H-indol-3-yl](cyclopropyl)methylidene]hydrazinecarboximidamide,
2-{1-[1-(butylsulfonyl)-5-chloro-1H-indol-3-yl]ethylidene}hydrazinecarboximidamide,
2-{1-[1-(butylsulfonyl)-5-chloro-1H-indol-3-yl]pentylidene}hydrazinecarboximidamide,
2-[[1-(butylsulfonyl)-5-chloro-1H-indol-3-yl](cyclopropyl)methylidene]hydrazinecarboximidamide,
2-(1-{5-chloro-1-[(4-methoxyphenyl)sulfonyl]-1H-indol-3-yl}ethylidene)hydrazinecarboximidamide.
2-(1-{5-chloro-1-[(4-methoxyphenyl)sulfonyl]-1H-indol-3-yl}pentylidene)hydrazinecarboximidamide,
2-[{5-chloro-1-[(4-methoxyphenyl)sulfonyl]-1H-indol-3-yl}(cyclopropyl)methylidene]hydrazinecarboximidamide,
2-{1-[5-chloro-1-(2-naphthylsulfonyl)-1H-indol-3-yl]ethylidene}hydrazinecarboximidamide,
2-{1-[5-chloro-1-(2-naphthylsulfonyl)-1H-indol-3-yl]pentylidene}hydrazinecarboximidamide,
2-[[5-chloro-1-(2-naphthylsulfonyl)-1H-indol-3-yl](cyclopropyl)methylidene]hydrazinecarboximidamide,
2-{1-[5-chloro-1-(phenylsulfonyl)-1H-indol-3-yl]ethylidene}hydrazinecarboximidamide,
2-{1-[5-chloro-1-(phenylsulfonyl)-1H-indol-3-yl]pentylidene}hydrazinecarboximidamide,
2-[[5-chloro-1-(phenylsulfonyl)-1H-indol-3-yl](cyclopropyl)methylidene]hydrazinecarboximidamide,
2-(1-{5-chloro-1-[(3,4-dimethoxyphenyl)sulfonyl]-1H-indol-3-yl}ethylidene)hydrazinecarboximidamide,
2-(1-{5-chloro-1-[(3,4-dimethoxyphenyl)sulfonyl]-1H-indol-3-yl}pentylidene)hydrazinecarboximidamide,
2-[{5-chloro-1-[(3,4-dimethoxyphenyl)sulfonyl]-1H-indol-3-yl}(cyclopropyl)-methylidene]hydrazinecarboximidamide,
2-{1-[2-(4-chlorophenyl)-1-(methylsulfonyl)-1H-indol-3-yl]ethylidene}hydrazinecarboximidamide,
2-{1-[2-(4-chlorophenyl)-1-(methylsulfonyl)-1H-indol-3-yl]pentylidene}hydrazinecarboximidamide,
2-[[2-(4-chlorophenyl)-1-(methylsulfonyl)-1H-indol-3-yl](cyclopropyl)methylidene]hydrazinecarboximidamide,
2-[{2-(4-chlorophenyl)-1-[(4-methoxyphenyl)sulfonyl]-1H-indol-3-yl}(cyclopropyl)-methylidene]hydrazinecarboximidamide,
2-[[2-(4-chlorophenyl)-1-(2-naphthylsulfonyl)-1H-indol-3-yl](cyclopropyl)methylidene]hydrazinecarboximidamide,
2-{1-[2-(4-chlorophenyl)-1-(phenylsulfonyl)-1H-indol-3-yl]ethylidene}hydrazinecarboximidamide,
2-{1-[2-(4-chlorophenyl)-1-(phenylsulfonyl)-1H-indol-3-yl]pentylidene}hydrazinecarboximidamide,
2-[[2-(4-chlorophenyl)-1-(phenylsulfonyl)-1H-indol-3-yl](cyclopropyl)methylidene]hydrazinecarboximidamide,
2-(1-{2-(4-chlorophenyl)-1-[(3,4-dimethoxyphenyl)sulfonyl]-1H-indol-3-yl}ethylidene)hydrazinecarboximidamide,
2-[{2-(4-chlorophenyl)-1-[(3,4-dimethoxyphenyl)sulfonyl]-1H-indol-3-yl}(cyclopropyl)-methylidene]hydrazinecarboximidamide,
2-{1-[6-fluoro-1-(methylsulfonyl)-1H-indol-3-yl]ethylidene}hydrazinecarboximidamide,
2-{1-[6-fluoro-1-(methylsulfonyl)-1H-indol-3-yl]pentylidene}hydrazinecarboximidamide,
2-{cyclopropyl[6-fluoro-1-(methylsulfonyl)-1H-indol-3-yl]methylidene}hydrazinecarboximidamide,
2-{1-[1-(butylsulfonyl)-6-fluoro-1H-indol-3-yl]ethylidene}hydrazinecarboximidamide,
2-{1-[1-(butylsulfonyl)-6-fluoro-1H-indol-3-yl]pentylidene}hydrazinecarboximidamide,
2-[[1-(butylsulfonyl)-6-fluoro-1H-indol-3-yl](cyclopropyl)methylidene]hydrazinecarboximidamide,
2-(1-{6-fluoro-1-[(4-methoxyphenyl)sulfonyl]-1H-indol-3-yl}ethylidene)hydrazinecarboximidamide,
2-(1-{6-fluoro-1-[(4-methoxyphenyl)sulfonyl]-1H-indol-3-yl}pentylidene)hydrazinecarboximidamide,
2-(cyclopropyl{6-fluoro-1-[(4-methoxyphenyl)sulfonyl]-1H-indol-3-yl}methylidene)hydrazinecarboximidamide,
2-{1-[6-fluoro-1-(2-naphthylsulfonyl)-1H-indol-3-yl]ethylidene}hydrazinecarboximidamide,
2-{1-[6-fluoro-1-(2-naphthylsulfonyl)-1H-indol-3-yl]pentylidene}hydrazinecarboximidamide,
2-{cyclopropyl[6-fluoro-1-(2-naphthylsulfonyl)-1H-indol-3-yl]methylidene}hydrazinecarboximidamide,
2-{1-[6-fluoro-1-(phenylsulfonyl)-1H-indol-3-yl]ethylidene}hydrazinecarboximidamide,
2-{1-[6-fluoro-1-(phenylsulfonyl)-1H-indol-3-yl]pentylidene}hydrazinecarboximidamide,
2-{cyclopropyl[6-fluoro-1-(phenylsulfonyl)-1H-indol-3-yl]methylidene}hydrazinecarboximidamide,
2-(1-{1-[(3,4-dimethoxyphenyl)sulfonyl]-6-fluoro-1H-indol-3-yl}ethylidene)hydrazinecarboximidamide,
2-(1-{1-[(3,4-dimethoxyphenyl)sulfonyl]-6-fluoro-1H-indol-3-yl}pentylidene)hydrazinecarboximidamide, 2-(cyclopropyl{1-[(3,4-dimethoxyphenyl)sulfonyl]-6-fluoro-1H-indol-3-yl}methylidene)hydrazinecarboximidamide,
2-{1-[5-fluoro-1-(phenylsulfonyl)-1H-indol-3-yl]propylidene}hydrazinecarboximidamide,
2-(1-{1-[(4-aminophenyl)sulfonyl]-5-fluoro-1H-indol-3-yl}propylidene)hydrazinecarboximidamide,
2-{1-[5-fluoro-1-(2-naphthylsulfonyl)-1H-indol-3-yl]propylidene}hydrazinecarboximidamide,
2-(1-{1-[(4-aminophenyl)sulfonyl]-5-chloro-1H-indol-3-yl}propylidene)hydrazinecarboximidamide,
2-{1-[5-chloro-1-(2-naphthylsulfonyl)-1H-indol-3-yl]propylidene}hydrazinecarboximidamide,
N-pentyl-2-{1-[1-(phenylsulfonyl)-1H-indol-3-yl]ethylidene}hydrazinecarboximidamide,
2-{1-[1-(phenylsulfonyl)-1H-indol-3-yl]ethylidene}-N-propylhydrazinecarboximidamide,
N-benzyl-2-{1-[1-(phenylsulfonyl)-1H-indol-3-yl]ethylidene}hydrazinecarboximidamide,
2-{1-[1-(phenylsulfonyl)-1H-indol-3-yl]ethylidene}-N-(pyridin-2-ylmethyl)hydrazinecarboximidamide,
N-(2-hydroxyethyl)-2-{1-[1-(phenylsulfonyl)-1H-indol-3-yl]ethylidene}hydrazinecarboximidamide,
2-[6-chloro-9-(phenylsulfonyl)-1,2,3,9-tetrahydro-4H-carbazol-4-ylidene]-hydrazinecarboximidamide,
2-[6-chloro-9-(phenylsulfonyl)-1,2,3,9-tetrahydro-4H-carbazol-4-one 4,5-dihydro-1H-imidazol-2-ylhydrazone,
2-[6-chloro-9-(phenylsulfonyl)-1,2,3,9-tetrahydro-4H-carbazol-4-one 4,5-dihydro-1H-imidazol-2-yl(methyl)hydrazone,
2-[9-(phenylsulfonyl)-1,2,3,9-tetrahydro-4H-carbazol-4-ylidene]hydrazinecarboximidamide,
2-[6-bromo-9-(phenylsulfonyl)-1,2,3,9-tetrahydro-4H-carbazol-4-one 4,5-dihydro-1H-imidazol-2-ylhydrazone,
2-[6-bromo-9-(phenylsulfonyl)-1,2,3,9-tetrahydro-4H-carbazol-4-one 4,5-dihydro-1H-imidazol-2-yl(methyl)hydrazone,
2-[6-bromo-9-(phenylsulfonyl)-1,2,3,9-tetrahydro-4H-carbazol-4-ylidene]hydrazinecarboximidamide,
2-[6-chloro-9-(methylsulfonyl)-1,2,3,9-tetrahydro-4H-carbazol-4-ylidene]hydrazinecarboximidamide,
2-{6-chloro-9-[(4-methoxyphenyl)sulfonyl]-1,2,3,9-tetrahydro-4H-carbazol-4-ylidene}hydrazinecarboximidamide,
2-{9-[(2-amino-4-methyl-1,3-thiazol-5-yl)sulfonyl]-6-chloro-1,2,3,9-tetrahydro-4H-carbazol-4-ylidene}hydrazinecarboximidamide,
2-[6-chloro-9-(2-naphthylsulfonyl)-1,2,3,9-tetrahydro-4H-carbazol-4-ylidene]hydrazinecarboximidamide,
2-{6-chloro-9-[(3,4-dimethoxyphenyl)sulfonyl]-1,2,3,9-tetrahydro-4H-carbazol-4-ylidene}hydrazinecarboximidamide, or the stereoisomers thereof, the tautomers thereof or the pharmaceutically acceptable salts thereof.

Compounds of the invention may be prepared using conventional synthetic methods and, if required, standard separation and isolation techniques. For example, compounds of formula I wherein Q is $SO_2$ and $R_8$ is H (Ia) may be prepared by reacting a compound of formula II with dimethylformamide (DMF) and phosporous oxychloride to give the 3-carboxaldehyde of formula III, sulfonylating the formula III compound with the appropriate sulfonyl chloride, $ClSO_2R_{10}$, in the presence of a base such as NaH to give the sulfonylated compound of formula IV and reacting the formula IV compound with an aminoguanidine derivative of formula V to give the desired product of formula Ia. The reaction sequence is shown in flow diagram I.

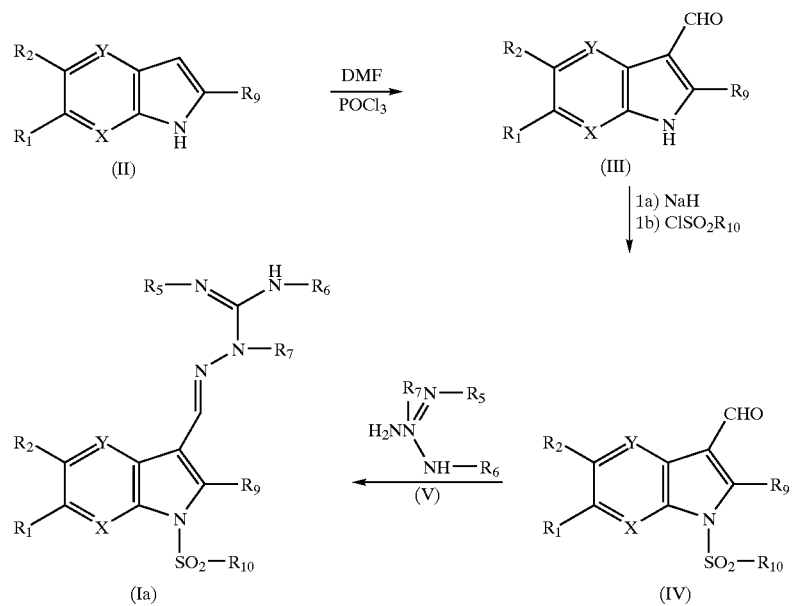

Similarly, compounds of formula I wherein Q is $SO_2$ and $R_8$ is an optionally substituted alkyl or cycloalkyl group (Ib) may be prepared by acylating a formula II compound with an acyl halide, $R_8CO$-Hal, to give the 3-acyl compound of formula VI, sulfonylating the formula VI compound, and reacting the sulfonylated product with an aminoguanidine derivative of formula V, as described in flow diagram II, to give the desired formula Ib product. The reaction is shown in flow diagram II wherein Hal represents Cl, Br or I.

Flow Diagram II

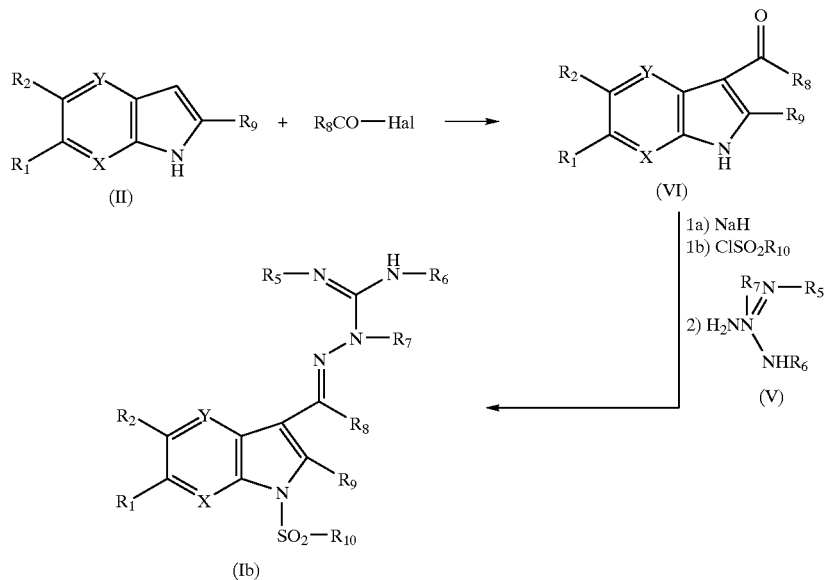

Compounds of formula I wherein Q is $SO_2$ and $R_8$ and $R_9$ are taken together with the atoms to which they are attached to form an optionally substituted six-membered ring (Ic) may be prepared by reacting 1,3-cyclohexanedione with a hydrazine of formula VII to form the hydrazone of formula VIII, heating said formula VIII hydrazone in the presence of trifluoroacetic acid (TFA) to form the 4-oxocarbazole of formula IX, and sequentially sulfonylating the formula IV compound and reacting the sulfonylated product with an aminoguanidine derivative as described hereinabove to give the desired compound of formula Ic. The reaction scheme is shown in flow diagram III.

Flow Diagram III

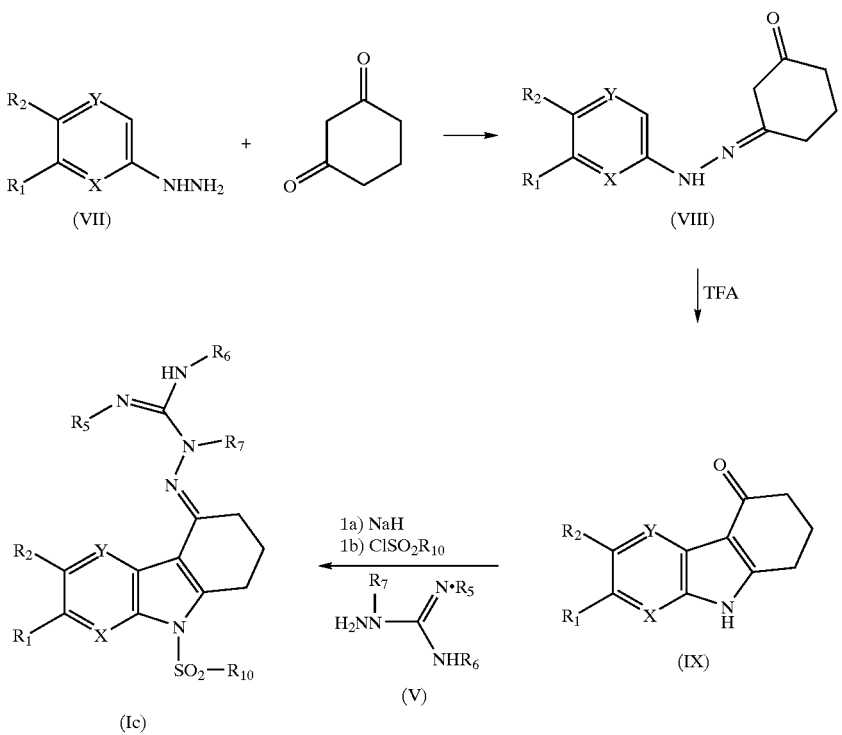

Compounds of formula I wherein $R_8$ and $R_9$ are taken together to form a 5- or 7-membered ring (Id) may be prepared by the regioselective oxidation of a ring fused indole system as described by Oikawa et al, Heterocyclic, 1976, 4, 1959 and Comp. Het. Chem., 1984, 4, 253 to give the intermediate of formula X which may be converted to the desired formula (Id) product. The reaction scheme is shown in flow diagram IV wherein n is 1, 2 or 3.

Flow Diagram IV

Compounds of formula I wherein Q is CO, $CO_2$, $CONR_{11}$ or $CSNR_{12}$ may be prepared by reacting the intermediates of formulas III, VI, IX or X with the appropriate acylhalide, α-haloester, isocyanate or isothiocyanate, respectively.

Azainodoles such as 4-azaindole or 7-azaindole may be prepared by methods described in the literature, i.e., I. Mahadevan, I., Rasmussen, M., J. Het. Chem., 1992, 29, 359–367; Hands, D.; Bishop, B.; Cameron, M.; Edwards, J. S.; Cottrell, I. F.; Wright, S. H. B., Synthesis, 1996, 877–882; Dobson, D.; Todd, A.; Gilmore, J., Synth. Commum. 1991, 21, 611–167. In addition, azaindoles are also available commercially.

Sulfonyl chlorides, $R_{10}SO_2Cl$, may be obtained commercially or prepared by conventional techniques. For example, 6-substituted-imidazo[2,1-b][1,3]thiazol-5-yl sulfonyl chlorides of formulas XIIIa and XIIIb may be prepared by reacting 2-amino-thiazole with chloroacetic acid or a suitable chloromethyl ketone to give 2-imino-4-thiazolin-3-ylacetic acid (XIa) or the 2-imino-4-thiazolin-3-yl ketone (XIb), respectively; reacting either XIa or XIb with $POCl_3$ to give, in the case of XIa, 6-chloroimidazo[2,1-b]thiazole (XIIa) or, in the case of XIb, 6-substituted-imidazo[2,1-b] thiazole XIIb; and sequentially reacting the respective XIIa and XIIb compounds with chlorosulfonic acid and $POCl_3$ to give the desired sulfonyl chlorides of formulas XIIIa and XIIIb. The reactions are illustrated in flow diagram V wherein R represents an optional substituent as described hereinabove with the exclusion of halogen.

Flow Diagram V

Advantageously, the present invention provides a process for the preparation of a compound of formula I which comprises reacting a compound of formula XIV with an aminoguanidine derivative of formula V in the presence of an acid, optionally in the presence of a solvent. The process is shown in flow diagram VI.

Flow Diagram VI

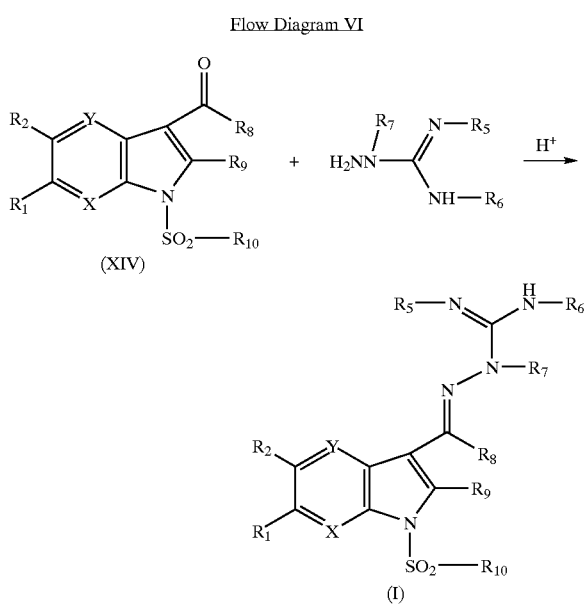

Acids suitable for use in the process of the invention include acids such as HCl, HBr, $H_2SO_4$, $HNO_2$ or the like, preferably HCl. Solvents suitable for use in the process of invention include protic solvents such as lower alkyl alcohols, i.e., methanol, ethanol, isopropanol, propanol or the like, preferably isopropanol.

Advantageously, the inventive compound of formula I may be utilized in the treatment of central nervous system disorders relating to or affected by the 5-HT6 receptor such as motor, mood, psychiatric, cognitive, neurodegenerative, or the like disorders, for example, Alzheimer's disease, Parkinson's disease, attention deficit disorder, anxiety, epilepsy, depression, obsessive compulsive disorder, migraine, sleep disorders, neurodegenerative disorders (such as head trauma or stroke), feeding disorders (such as anorexia or bulimia), schizophrenia, memory loss, disorders associated with withdrawal from drug or nicotine abuse, or the like or certain gastrointestinal disorders such as irritable bowel syndrome. Accordingly, the present invention provides a method for the treatment of a disorder of the central nervous system (CNS) related to or affected by the 5-HT6 receptor in a patient in need thereof which comprises providing said patient a therapeutically effective amount of a compound of formula I

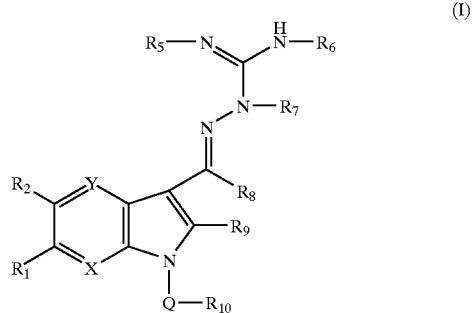

wherein

X is N or $CR_3$;

Y is N or $CR_4$;

Q is $SO_2$, CO, $CO_2$, CONR or $CSNR_{12}$;

$R_1, R_2, R_3$ and $R_4$ are each independently H, halogen, CN, $OCO_2R_{13}$, $CO_2R_{14}$, $CONR_{15}R_{16}$, $NR_{17}SO_2R_{18}$, $NR_{19}COR_{28}$, $SO_nR_{20}$, $NR_{21}R_{22}$, $OR_{23}$, $COR_{24}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_5, R_6$ and $R_7$ are each independently H or a $C_1$–$C_6$alkyl, $C_2$–$C_6$alkenyl, $C_2$–$C_6$alkynyl, $C_3$–$C_{12}$cycloalkyl, cycloheteroalkyl, aryl or heteroaryl group each optionally substituted or $R_5$ and $R_6$ maybe taken together with the atoms to which they are attached to form an optionally substituted 5- to 7-membered ring;

$R_8$ is H or a $C_1$–$C_6$alkyl or $C_3$–$C_{10}$cycloalkyl group each optionally substituted;

$R_9$ is H, halogen, CN, $NO_2$, $NR_{25}R_{26}$, $OR_{27}$ or a $C_1$–$C_6$alkyl, aryl or heteroaryl group each optionally substituted or $R_8$ and $R_9$ may be taken together with the atoms to which they are attached to form an optionally substituted 5- to 7-membered ring optionally containing one or two heteroatoms selected from O, N or S;

$R_{10}$ is a $C_1$–$C_6$alkyl, aryl or heteroaryl group each optionally substituted or an optionally substituted 8- to 13-membered bicyclic or tricyclic ring system having a N atom at the bridgehead and optionally containing 1, 2 or 3 additional heteroatoms selected from N, O or S with the proviso that when $R_8$ is H or $C_1$–$C_6$alkyl and Q is CO then $R_{10}$ must be other than $C_1$–$C_6$alkyl or aryl;

n is 0 or an integer of 1 or 2;

$R_{11}$ and $R_{12}$ are each independently H or a $C_1$–$C_6$alkyl, aryl or heteroaryl group each optionally substituted;

$R_{13}, R_{14}, R_{18}, R_{20}, R_{23}, R_{24}, R_{27}$ and $R_{28}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{15}$ and $R_{16}$ are each independently H or an optionally substituted $C_1$–$C_6$alkyl group; and $R_{17}, R_{19}, R_{21}, R_{22}, R_{25}$ and $R_{26}$ are each independently H or an optionally substituted $C_1$–$C_4$alkyl group or $R_{21}$ and $R_{22}$ may be taken together with the atom to which they are attached to form a 5- to 7-membered ring optionally containing another heteroatom selected from O, N or S; or the stereoisomers thereof, the tautomers thereof or the pharmaceutically acceptable salts thereof.

The term "providing" as used herein with respect to providing a compound or substance covered by the invention, designates either directly administering such a compound or substance, or administering a prodrug, derivative or analog which forms an equivalent amount of the compound or substance within the body.

The compounds of formula I may be provided by oral or parenteral administration or in any common manner known to be an effective administration of a therapeutic agent to a patient in need thereof.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I

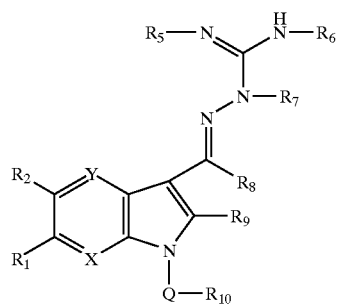

(I)

wherein

X is N or $CR_3$;

Y is N or $CR_4$;

Q is $SO_2$, CO, $CO_2$, $CONR_{11}$ or $CSNR_{12}$;

$R_1$, $R_2$, $R_3$ and $R_4$ are each independently H, halogen, CN, $OCO_2R_{13}$, $CO_2R_{14}$, $CONR_{15}R_{16}$, $NR_{17}SO_2R_{18}$, $NR_{19}COR_{28}$, $SO_nR_{20}$, $NR_{21}R_{22}$, $OR_{23}$, $COR_{24}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_5$, $R_6$ and $R_7$ are each independently H or a $C_1$–$C_6$alkyl, $C_2$–$C_6$alkenyl, $C_2$–$C_6$alkynyl, $C_3$–$C_{12}$cycloalkyl, cycloheteroalkyl, aryl or heteroaryl group each optionally substituted or $R_5$ and $R_6$ maybe taken together with the atoms to which they are attached to form an optionally substituted 5- to 7-membered ring;

$R_8$ is H or a $C_1$–$C_6$alkyl or $C_3$–$C_{10}$cycloalkyl group each optionally substituted;

$R_9$ is H, halogen, CN, $NO_2$, $NR_{25}R_{26}$, $OR_{27}$ or a $C_1$–$C_6$alkyl, aryl or heteroaryl group each optionally substituted or $R_8$ and $R_9$ may be taken together with the atoms to which they are attached to form an optionally substituted 5- to 7-membered ring optionally containing one or two heteroatoms selected from O, N or S;

$R_{10}$ is a $C_1$–$C_6$alkyl, aryl or heteroaryl group each optionally substituted or an optionally substituted 8- to 13-membered bicyclic or tricyclic ring system having a N atom at the bridgehead and optionally containing 1, 2 or 3 additional heteroatoms selected from N, O or S with the proviso that when $R_8$ is H or $C_1$–$C_6$alkyl and Q is CO then $R_{10}$ must be other than $C_1$–$C_6$alkyl or aryl;

n is 0 or an integer of 1 or 2;

$R_{11}$ and $R_{12}$ are each independently H or a $C_1$–$C_6$alkyl, aryl or heteroaryl group each optionally substituted;

$R_{13}$, $R_{14}$, $R_{18}$, $R_{20}$, $R_{23}$, $R_{24}$, $R_{27}$ and $R_{28}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{15}$ and $R_{16}$ are each independently H or an optionally substituted $C_1$–$C_6$alkyl group; and $R_{17}$, $R_{19}$, $R_{21}$, $R_{22}$, $R_{25}$ and $R_{26}$ are each independently H or an optionally substituted $C_1$–$C_4$alkyl group or $R_{21}$ and $R_{22}$ may be taken together with the atom to which they are attached to form a 5- to 7-membered ring optionally containing another heteroatom selected from O, N or S; or the stereoisomers thereof, the tautomers thereof or the pharmaceutically acceptable salts thereof.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The term HPLC designates high performance liquid chromatography. The terms THF and DMSO designate tetrahydrofuran and dimethylsulfoxide, respectively.

EXAMPLE 1

Preparation of 1-[(4-methylphenyl)sulfonyl]-1H-indole-3-carboxaldehyde 1,4,5,6-tetrahydropyrimidin-2-ylhydrazone

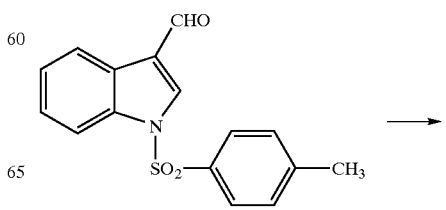

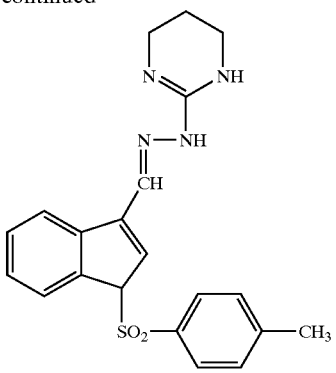

A stirred suspension of 1-[(4-methylphenyl)sulfonyl]indole-3-carboxaldehyde (74.8 mg, 0.25 mmol) in isopropanol is treated with 2-hydrazine-1,4,5,6-tetrahydropyrimidine hydrobromide (60.5 mg, 0.25 mmol) and concentrated HCl (5 μL), heated at 80° C. for 2 h, cooled to room temperature and concentrated in vacuo. The resultant residue is purified by HPLC to give the title product, 53.2 mg (42% yield), identified by HPLC[1] and mass spectral analyses.

[1]HPLC conditions: Hewlett Packard 1100; YMC ODS-A 4.6 mm×50 mm 5 u column at 23° C.; 10 uL injection; Solvent A: 0.05% TFA/water; Solvent B: 0.05% TFA/acetonitrile; Gradient: Time 0: 98% A; 1 min: 98% A; 7 min: 10% A, 8 min: 10% A; 8.9 min: 98% A; Post time 1 min. Flow rate 2.5 mL/min; Detection: 220 and 254 nm DAD.

EXAMPLE 2
Preparation of 2-{Cyclohexyl[1-(phenylsulfonyl)-1H-indol-3-yl]methylidene}-hydrazinecarboximidamide

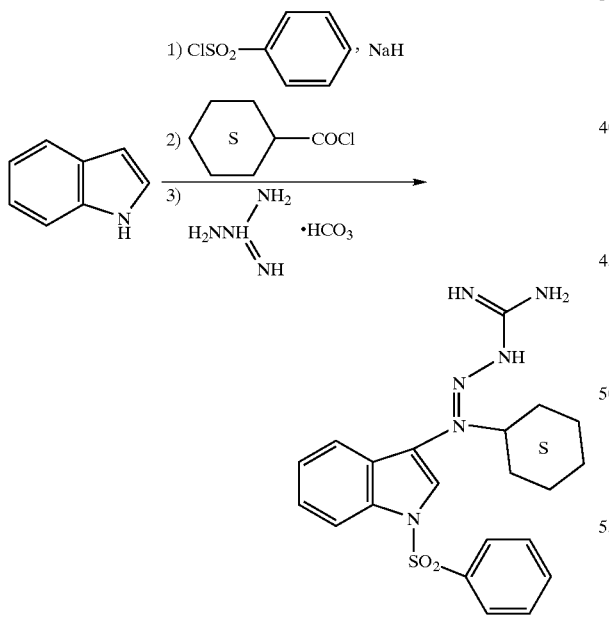

A solution of indole (11.7 g, 0.1 mol) in THF is added to a stirred mixture of NaH (60% dispersion in mineral oil, 4.2, g 0.105 mol), DMSO and THF. The reaction mixture is stirred for 1 h at room temperature, cooled to 0° C., treated with phenylsulfonyl chloride (13.3 mL, 0.15 mol), stirred at ambient temperatures for 3 h, quenched with water and extracted with ethyl acetate. The extracts are combined, dried over $MgSO_4$ and concentrated in vacuo. The resultant residue is crystallized in ethanol and filtered. The filtercake is air-dried to give 1-phenylsulfonylindole. A portion of this 1-phenylsulfonylindole (257 mg, 1.0 mmol) and cyclohexylcarbonyl chloride (0.175 mL, 1.3 mmol) in methylene chloride is treated with tin tetrachloride (97 μL, 1.9 mmol) at room temperature, shaken for 6 h, quenched with saturated $NaHCO_3$ and extracted with ethylacetate. The extracts are combined and concentrated in vacuo to give a residue. The residue is suspended in isopropanol, treated sequentially with concentrated HCl (50 μL) and aminoguanidine bicarbonate (100 mg, 0.5 mmol), heated at 80° C. for 4 h, cooled to room temperature and concentrated in vacuo. The resultant residue is purified by HPLC to afford the title product 37.7 mg (17% yield), identified by HPLC[1] and mass spectral analyses.

[1]HPLC conditions: Hewlett Packard 1100; YMC ODS-A 4.6 mm×50 mm 5 u column at 23° C.; 10 uL injection; Solvent A: 0.05% TFA/water; Solvent B: 0.05% TFA/acetonitrile; Gradient: Time 0: 98% A; 1 min: 98% A; 7 min: 10% A, 8 min: 10% A; 8.9 min: 98% A; Post time 1 min. Flow rate 2.5 mL/min; Detection: 220 and 254 nm DAD.

EXAMPLES 3–9

Preparation of 2-[1-(Arylsulfonyl)indol-3-y]carboxaldehyde hydrazone or Hydrazinecarboximidamide Derivatives

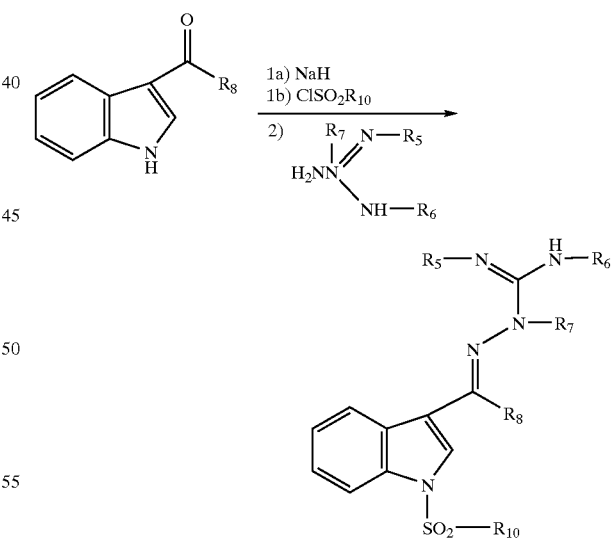

Using essentially the same procedures described in Examples 1 and 2 and substituting the appropriate arylsulfonyl chloride and aminoguanidine, the compounds shown on Table I are obtained and identified by HPLC and mass spectral analyses. HPLC conditions are the same as that used in Examples 1 and 2.

TABLE I

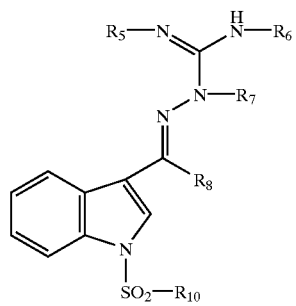

| EX NO | R5 | R6 | R7 | R8 | R10 | M + H | Time Min |
|---|---|---|---|---|---|---|---|
| 3 | H | H | H | H | 4-methylphenyl | 356 | 4.42 |
| 4 | —CH₂—CH₂— | | CH₃ | H | 4-methylphenyl | 396 | 4.52 |
| 5 | H | H | H | isopropyl | phenyl | 384 | 4.5 |
| 6 | H | H | H | benzyl | phenyl | 432 | 4.6 |
| 7 | H | H | H | isobutyl | phenyl | 398 | 4.6 |
| 8 | H | H | H | 2-chlorocinnamyl | phenyl | 478 | 5.2 |
| 9 | H | H | H | methyl | phenyl | 356 | 4.2 |

EXAMPLE 10

Preparation of 2{1-[5-Chloro-2-methyl-1-(phenylsulfonyl)-1H-indol-3-yl]ethylidene}hydrazinecarboxamidamide

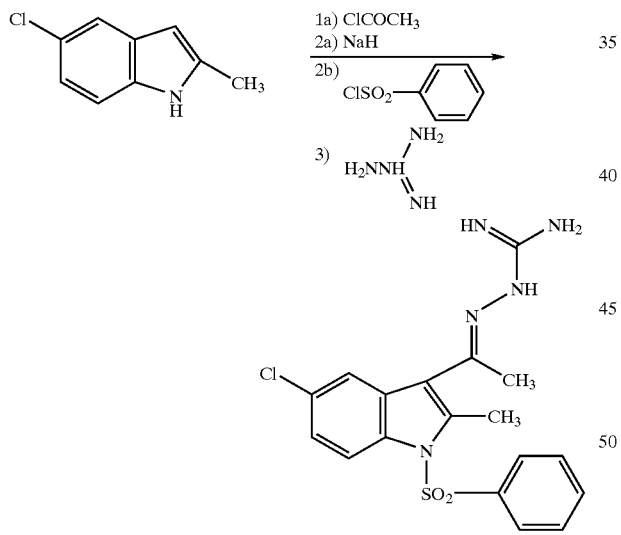

A mixture of 5-chloro-2-methylindole (248 mg, 0.5 mmol) and acetyl chloride (0.045 mL, 0.6 mmol) in methylene chloride is treated with a 1.0 M solution of tin tetrachloride in methylene chloride (0.55 µL, 0.55 mmol), shaken at room temperature for 6 h, quenched with saturated NaHCO₃ and extracted with ethyl acetate. The extracts are combined and concentrated in vacuo. The resultant residue and phenylsulfonyl chloride (0.095 mL, 0.75 mmol) are dissolved in THF, treated with NaH (60 mg, 1.5 mmol) at room temperature, shaken for 6 h, quenched with saturated NaHCO₃ and extracted with ethyl acetate. The extracts are combined and concentrated in vacuo to give a residue. This residue is suspended in isopropanol, treated sequentially with aminoguanidine bicarbonate (100 mg, 0.5 mmol) and concentrated HCl (50 µL), heated at 80° C. for 4 h, cooled to room temperature and concentrated in vacuo. This resultant residue is purified by HPLC to afford the title product, 10 mg (5% yield), identified by HPLC and mass spectral analyses, (M+H) 404; retention time 4.72 min.

EXAMPLES 11–122

Preparation of {[1-(Substituted-sulfonyl) indol-3-yl] alkylidene} hydrazinecarboximidamide derivatives

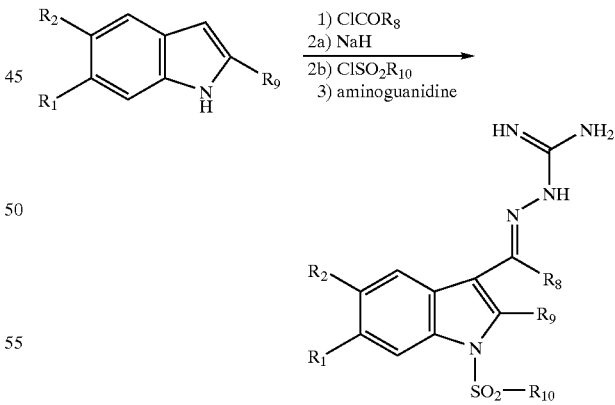

Using essentially the same procedures described in Examples 1, 2 and 10 and employing the appropriately substituted indole substrate, aryl or alkyl sulfonyl chloride and acyl halide, the compounds shown in Table II are obtained and identified by HPLC and mass spectral analyses. The HPLC conditions used are the same as that described for Example 1.

TABLE II

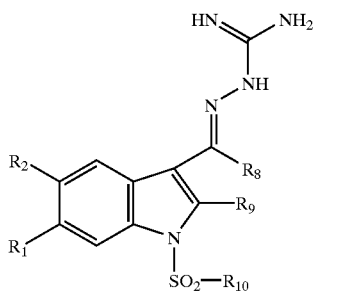

| EX NO | R1 | R2 | R8 | R9 | R10 | M + H | Time Min |
|---|---|---|---|---|---|---|---|
| 11 | H | H | CH₃ | 4-fluorophenyl | phenyl | 450 | 5.07 |
| 12 | H | H | CH₃ | 3-chloro-4-fluorophenyl | phenyl | 483 | 4.99 |
| 13 | H | H | CH₃ | 3,4-difluoro-phenyl | phenyl | 468 | 5.94 |
| 14 | H | H | CH₃ | 2-naphthyl | phenyl | 482 | 5.75 |
| 15 | H | H | CH₃ | Phenyl | phenyl | 432 | 4.95 |
| 16 | H | CN | CH₃ | H | phenyl | 381 | 4.30 |
| 17 | H | I | CH₃ | H | phenyl | 481 | 4.75 |
| 18 | H | NO₂ | CH₃ | H | phenyl | 401 | 4.42 |
| 19 | H | F | CH₃ | H | phenyl | 374 | 4.42 |
| 20 | H | OCH₃ | CH₃ | H | phenyl | 372 | 4.39 |
| 21 | H | OCH₂C₆H₅ | CH₃ | H | phenyl | 448 | 5.05 |
| 22 | H | H | CH₃ | H | 2-amino-4-methly-1,3-thiazol-5-yl | 392 | 3.96 |
| 23 | H | H | CH₃ | H | 4-aminophenyl | 371 | 4.10 |
| 24 | H | H | CH₃ | H | 2,1,3-benzothiodiazol-4-yl | 414 | 4.28 |
| 25 | H | H | CH₃ | H | 2,1,3-benzoxadiazol-4-yl | 398 | 4.28 |
| 26 | H | H | CH₃ | H | 4-biphenyl | 432 | 5.02 |
| 27 | H | H | CH₃ | H | 4-bromo-2,5-dichlorothien-3-yl | 510 | 4.91 |
| 28 | H | H | CH₃ | H | 4-bromo-5-chlorothien-2-yl | 474 | 5.01 |
| 29 | H | H | CH₃ | H | 3-bromo-5-chlorothien-2-yl | 474 | 5.00 |
| 30 | H | H | CH₃ | H | 4-bromophenyl | 434 | 4.64 |
| 31 | H | H | CH₃ | H | 2-bromophenyl | 434 | 4.41 |
| 32 | H | H | CH₃ | H | 3-bromophenyl | 434 | 4.63 |
| 33 | H | H | CH₃ | H | 5-bromothien-2-yl | 440 | 4.66 |
| 34 | H | H | CH₃ | H | 5-chloro-2-methoxyphenyl | 420 | 4.65 |
| 35 | H | H | CH₃ | H | 5-chloro-3-methyl-1-benzothien-2-yl | 460 | 5.23 |
| 36 | H | H | CH₃ | H | 6-chloroimidazo[2,1-b][1,3]-thiazol-5-yl | 436 | 4.32 |
| 37 | H | H | CH₃ | H | 5-chlorothien-2-yl | 396 | 4.63 |
| 38 | H | H | CH₃ | H | 5-dimethylamino-1-naphthyl | 449 | 4.78 |
| 39 | H | H | CH₃ | H | 4,5-dibromothien-2-yl | 519 | 4.65 |
| 40 | H | H | CH₃ | H | 2,5-dichorophenyl | 425 | 4.73 |
| 41 | H | H | CH₃ | H | 2,5-dichlorothien-3-yl | 431 | 4.76 |
| 42 | H | H | CH₃ | H | 2,3-dichlorothien-5-yl | 431 | 4.93 |
| 43 | H | H | CH₃ | H | 3,5-dimethylisoxazol-4-yl | 375 | 4.26 |
| 44 | H | H | CH₃ | H | 4-fluorophenyl | 374 | 4.42 |
| 45 | H | H | CH₃ | H | 5-[1-methyl-5-(trifluoromethyl)-1H-pyrazol-3-yl]thien-2-yl | 510 | 5.00 |
| 46 | H | H | CH₃ | H | 2-methyl-5-nitrophenyl | 415 | 4.56 |
| 47 | H | H | CH₃ | H | 1-methylimidazol-4-yl | 360 | 3.56 |
| 48 | H | H | CH₃ | H | 4-(methylsulfonyl)phenyl | 434 | 4.08 |
| 49 | H | H | CH₃ | H | 5-[2-(methylthio)pyrimidin-4-yl]thien-2-yl | 486 | 4.89 |
| 50 | H | H | CH₃ | H | 1-naphthyl | 406 | 4.68 |
| 51 | H | H | CH₃ | H | 2-nitrophenyl | 401 | 4.36 |
| 52 | H | H | CH₃ | H | 4-nitrophenyl | 401 | 4.45 |
| 53 | H | H | CH₃ | H | 5-pyridin-2-ylthien-2-yl | 439 | 4.68 |
| 54 | H | H | CH₃ | H | 4-(trifluoromethoxy)phenyl | 440 | 4.82 |
| 55 | H | H | CH₃ | H | methyl | 294 | 3.78 |
| 56 | H | H | n-C₄H₉ | H | methyl | 336 | 4.16 |
| 57 | H | H | Cyclopropyl | H | methyl | 320 | 3.69 |
| 58 | H | H | CH₃ | H | n-butyl | 336 | 4.74 |
| 59 | H | H | n-C₄H₉ | H | n-butyl | 378 | 5.34 |
| 60 | H | H | Cyclopropyl | H | n-butyl | 362 | 4.85 |
| 61 | H | H | CH₃ | H | 4-methoxyphenyl | 386 | 4.82 |
| 62 | H | H | n-C₄H₉ | H | 4-methoxyphenyl | 428 | 5.47 |
| 63 | H | H | Cyclopropyl | H | 4-methoxyphenyl | 412 | 4.99 |
| 64 | H | H | CH₃ | H | 2-naphthyl | 406 | 4.92 |
| 65 | H | H | n-C₄H₉ | H | 2-naphthyl | 448 | 5.72 |

TABLE II-continued

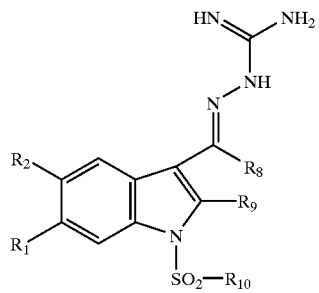

| EX NO | R1 | R2 | R8 | R9 | R10 | M + H | Time Min |
|---|---|---|---|---|---|---|---|
| 66 | H | H | Cyclopropyl | H | 2-naphthyl | 432 | 5.56 |
| 67 | H | H | n-C$_4$H$_9$ | H | phenyl | 398 | 4.78 |
| 68 | H | H | Cyclopropyl | H | phenyl | 382 | 4.57 |
| 69 | H | H | CH$_3$ | H | 3,4-dimethoxyphenyl | 416 | 4.39 |
| 70 | H | H | n-C$_4$H$_9$ | H | 3,4-dimethoxyphenyl | 458 | 5.02 |
| 71 | H | H | Cyclopropyl | H | 3,4-dimethoxyphenyl | 442 | 4.96 |
| 72 | H | Cl | CH$_3$ | H | methyl | 328 | 3.92 |
| 73 | H | Cl | n-C$_4$H$_9$ | H | methyl | 370 | 4.50 |
| 74 | H | Cl | Cyclopropyl | H | methyl | 354 | 4.73 |
| 75 | H | Cl | CH$_3$ | H | butyl | 370 | 5.02 |
| 76 | H | Cl | n-C$_4$H$_9$ | H | butyl | 412 | 5.78 |
| 77 | H | Cl | Cyclopropyl | H | butyl | 396 | 5.34 |
| 78 | H | Cl | CH$_3$ | H | 4-methoxyphenyl | 420 | 5.17 |
| 79 | H | Cl | n-C$_4$H$_9$ | H | 4-methoxyphenyl | 462 | 5.72 |
| 80 | H | Cl | Cyclopropyl | H | 4-methoxyphenyl | 446 | 5.39 |
| 81 | H | Cl | CH$_3$ | H | 2-naphthyl | 440 | 5.30 |
| 82 | H | Cl | n-C$_4$H$_9$ | H | 2-naphthyl | 483 | 5.83 |
| 83 | H | Cl | Cyclopropyl | H | 2-naphthyl | 466 | 5.56 |
| 84 | H | Cl | CH$_3$ | H | phenyl | 390 | 4.53 |
| 85 | H | Cl | n-C$_4$H$_9$ | H | phenyl | 432 | 5.08 |
| 86 | H | Cl | Cyclopropyl | H | phenyl | 416 | 4.66 |
| 87 | H | Cl | CH$_3$ | H | 3,4-dimethoxyphenyl | 450 | 5.21 |
| 88 | H | Cl | n-C$_4$H$_9$ | H | 3,4-dimethoxyphenyl | 493 | 5.32 |
| 89 | H | Cl | Cyclopropyl | H | 3,4-dimethoxyphenyl | 476 | 5.02 |
| 90 | H | H | CH$_3$ | 4-chlorophenyl | methyl | 404 | 4.92 |
| 91 | H | H | n-C$_4$H$_9$ | 4-chlorophenyl | methyl | 446 | 5.41 |
| 92 | H | H | Cyclopropyl | 4-chlorophenyl | methyl | 430 | 4.63 |
| 93 | H | H | Cyclopropyl | 4-chlorophenyl | 4-methoxyphenyl | 523 | 5.71 |
| 94 | H | H | Cyclopropyl | 4-chlorophenyl | 2-naphthyl | 543 | 5.86 |
| 95 | H | H | CH$_3$ | 4-chlorophenyl | phenyl | 466 | 4.90 |
| 96 | H | H | n-C$_4$H$_9$ | 4-chlorophenyl | phenyl | 509 | 5.56 |
| 97 | H | H | Cyclopropyl | 4-chlorophenyl | phenyl | 493 | 5.27 |
| 98 | H | H | CH$_3$ | 4-chlorophenyl | 3,4-dimethoxyphenyl | 527 | 5.37 |
| 99 | H | H | Cyclopropyl | 4-chlorophenyl | 3,4-dimethoxyphenyl | 553 | 5.56 |
| 100 | F | H | CH$_3$ | H | methyl | 312 | 3.94 |
| 101 | F | H | n-C$_4$H$_9$ | H | methyl | 354 | 4.4 |
| 102 | F | H | Cyclopropyl | H | methyl | 338 | 4.15 |
| 103 | F | H | CH$_3$ | H | n-butyl | 354 | 4.86 |
| 104 | F | H | n-C$_4$H$_9$ | H | n-butyl | 396 | 5.62 |
| 105 | F | H | Cyclopropyl | H | n-butyl | 380 | 5.17 |
| 106 | F | H | CH$_3$ | H | 4-methoxyphenyl | 404 | 5.02 |
| 107 | F | H | n-C$_4$H$_9$ | H | 4-methoxyphenyl | 446 | 5.12 |
| 108 | F | H | Cyclopropyl | H | 4-methoxyphenyl | 430 | 4.76 |
| 109 | F | H | CH$_3$ | H | 2-naphthyl | 424 | 5.32 |
| 110 | F | H | n-C$_4$H$_9$ | H | 2-naphthyl | 466 | 5.34 |
| 111 | F | H | Cyclopropyl | H | 2-naphthyl | 450 | 4.80 |
| 112 | F | H | CH$_3$ | H | phenyl | 374 | 4.45 |
| 113 | F | H | n-C$_4$H$_9$ | H | phenyl | 416 | 5.34 |
| 114 | F | H | Cyclopropyl | H | phenyl | 400 | 4.61 |
| 115 | F | H | CH$_3$ | H | 3,4-dimethoxyphenyl | 434 | 4.97 |
| 116 | F | H | n-C$_4$H$_9$ | H | 3,4-dimethoxyphenyl | 476 | 5.64 |
| 117 | F | H | Cyclopropyl | H | 3,4-dimethoxyphenyl | 460 | 4.76 |
| 118 | H | F | C$_2$H$_5$ | H | phenyl | 388 | — |
| 119 | H | F | C$_2$H$_5$ | H | 4-aminophenyl | 403 | — |
| 120 | H | F | C$_2$H$_5$ | H | 2-naphthyl | 438 | — |
| 121 | H | Cl | C$_2$H$_5$ | H | 4-aminophenyl | 419 | — |
| 122 | H | Cl | C$_2$H$_5$ | H | 2-naphthyl | 454 | — |

EXAMPLE 123

Preparation of N-Pentyl-2-{1-[1-(phenylsulfonyl)-1H-indol-3-yl]ethylidene}-hydrazinecarboximidamide

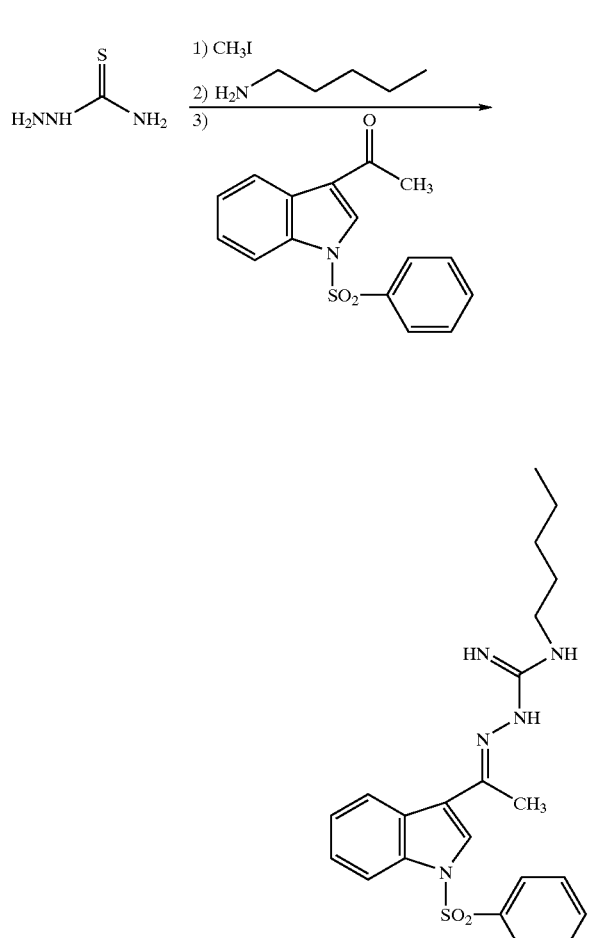

A solution of thiosemicarbazide (2.73 g, 30 mmol) in ethanol is treated with methyl iodate (1.96 mL, 31.5 mmol), heated at 60° C. for 1 h, cooled to room temperature, stored at −20° C. for 18 h and filtered. The filtercake is washed with cold ethanol and dried in vacuo. The thus-obtained S-methylisothiosemicarbazide hydrogen iodide (46.6 mg, 0.2 mmol) is dissolved in methanol, treated with pentylamine (24 μL, 0.22 mmol), heated at 60° C. for 2 h, cooled to room temperature and concentrated in vacuo. The resultant residue, 4-pentylaminoguanidine hydrogen iodide (0.2 mmol), is suspended in isopropanol, added to a suspension of 3-acetyl-N-(phenylsulfonyl) indole (59 mg, 0.2 mmol) in isopropanol and concentrated HCl (50 μL), heated at 80° C. for 4 h, cooled to room temperature and concentrated in vacuo to give a residue. This residue is purified by HPLC to give the title product, 17.9 mg (21% yield), identified by HPLC and mass spectral analyses, (M+H) 426; retention time 4.75 min.

EXAMPLES 124–127

Preparation of N-Substituted-2-{1-[(phenylsulfonyl)-1H-indole-3-yl]ethylidene}hydrazinecarboximidamide

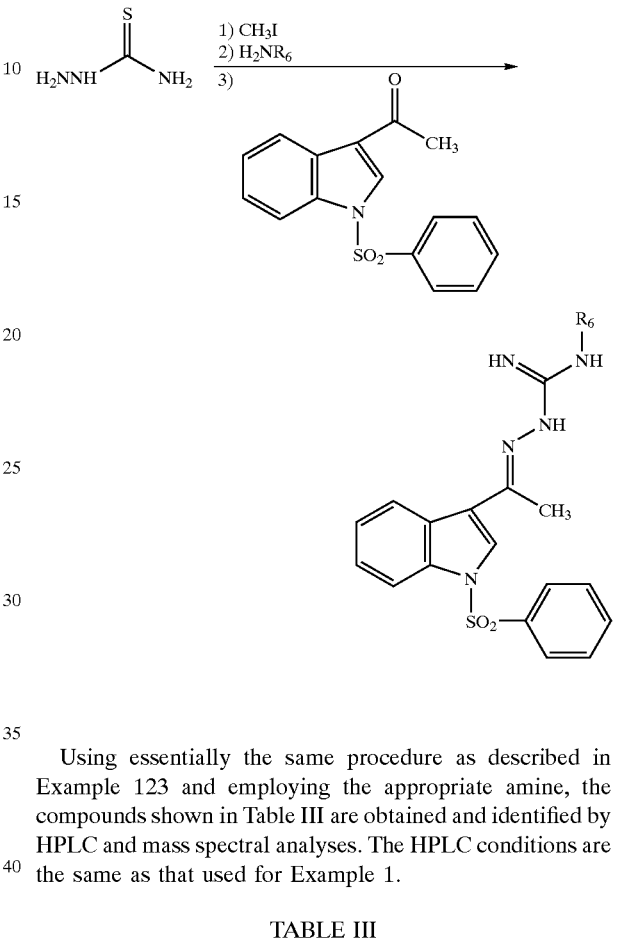

Using essentially the same procedure as described in Example 123 and employing the appropriate amine, the compounds shown in Table III are obtained and identified by HPLC and mass spectral analyses. The HPLC conditions are the same as that used for Example 1.

TABLE III

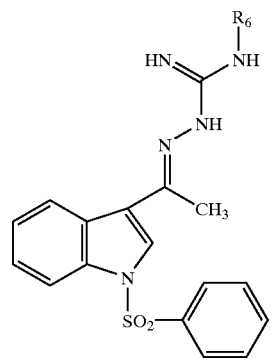

| Ex No. | R6 | M + H | Time Min. |
|---|---|---|---|
| 124 | n-propyl | 398 | 5.08 |
| 125 | benzyl | 446 | 4.91 |
| 126 | Pyridin-2-ylmethyl | 447 | 4.54 |
| 127 | 2-hydroxyethyl | 400 | 4.23 |

EXAMPLES 128–130

Preparation of 2[1-(1-Substituted-1H-indol-3-yl)ethylidene]hydrazinecarboximidamide

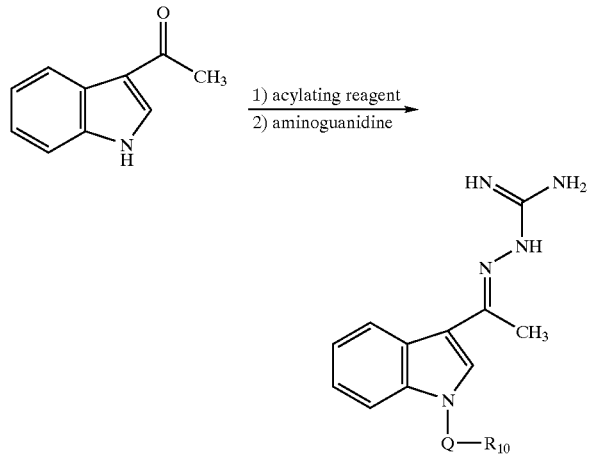

Using essentially the same procedure described in Example 10 and employing phenyl chloroformate, phenyl isocyanate or benzoyl chloride in place of ClSO$_2$R$_{10}$, the compounds shown in Table IV are obtained and identified by HPLC and mass spectral analyses.

TABLE IV

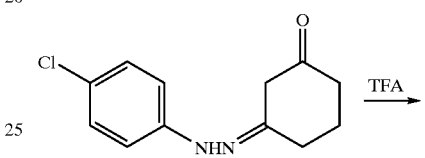

| Ex No. | Q | R10 | M + H | Time Min. |
|---|---|---|---|---|
| 128 | CO$_2$ | phenyl | 336 | 4.52 |
| 129 | CONH | phenyl | 335 | 4.39 |
| 130 | CO | phenyl | 320 | 3.32 |

EXAMPLE 131

Preparation of Cyclohexane-1,3-dione mono-(4-chlorophenyl)hydrazone

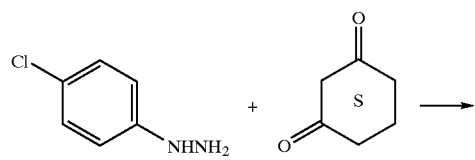

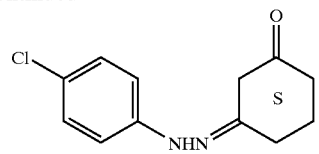

A solution of 1,3-cyclohexanedione (5.05 g, 45 mmol) in water is treated over a 10 min period with an aqueous suspension of p-chlorophenylhydrazine (8.06 g, 45 mmol), stirred at room temperature for 16 h and filtered. The filtercake is washed with water and dried in vacuo to give the title product which is used as in Example 132.

EXAMPLE 132

Preparation of 6-Chloro-4-oxo-1,2,3,4-tetrahydrocarbazole

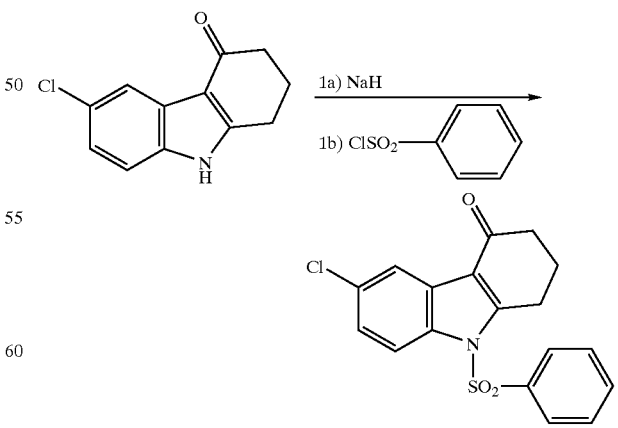

A mixture of cyclohexane-1,3-dione mono-(4-chlorophenyl) hydrazone (45 mmol) obtained in Example 131 and trifluoroacetic acid (30 mL) is heated to 80° C. for 16 h, cooled to room temperature, poured over ice water and filtered. The filtercake is dried and recrystallized from ethanol/water to afford the title product, 4.2 g (42% yield), identified by HPLC and mass spectral analyses.

EXAMPLE 133

Preparation of 6-chloro-1-(phenylsulfonyl)-4-oxo-1,2,3,4-tetrahydrocarbazole

A solution of 6-chloro-4-oxo-1,2,3,4-tetrahydrocarbazole (109 mg, 0.5 mmol) in THF is treated with NaH (60 mg, 60% dispersion in mineral oil, 1.5 mmol), stirred for 30 min., treated with phenylsulfonyl chloride (132 mg, 0.5 mmol), shaken for 8 h and concentrated in vacuo. The resultant residue is dissolved in ethyl acetate, washed with water and reconcentrated in vacuo to afford the title product which is used as is in Example 134.

EXAMPLE 134

Preparation of 2-[6-Chloro-9-(phenylsulfonyl)-1,2,3,9-tetrahydro-4H-carbazol-4-ylidene]hydrazinecarboximidamide

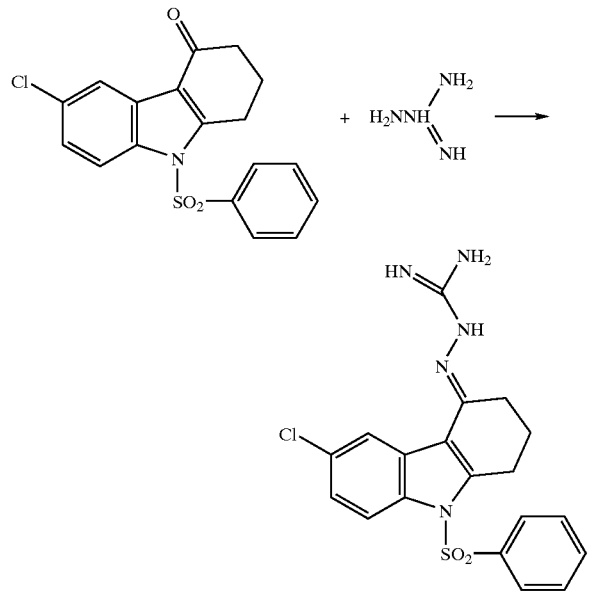

A suspension of 6-chloro-1-(phenylsulfonyl)-4-oxo-1,2,3,4-tetrahydrocarbazole (0.5 mmol) obtained in Example 133 in isopropanol and concentrated HCl (50 μL) is treated with aminoguanidine bicarbonate (66 mg, 0.5 mmol), heated at 80° C. for 4 h, cooled to room temperature and concentrated in vacuo. The resultant residue is purified by HPLC to afford the title product, 15.8 mg (7% yield), identified by HPLC and mass spectral analyses, (M+H) 416; retention time 4.49 min.

EXAMPLES 135–142

Preparation of 2-[6-Substituted-9-(arylsulfonyl)-1,2,3,9-tetrahydro-4H-carbazol-4-ylidene]hydrazine carboximidamide derivatives

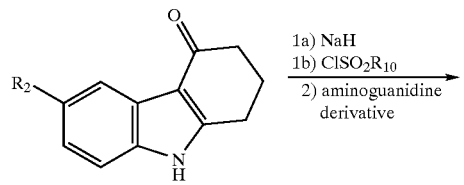

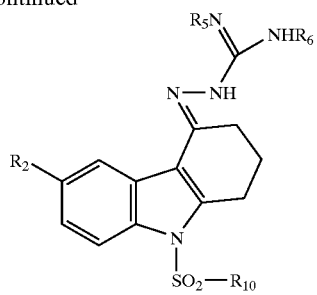

Using essentially the same procedures described in Examples 132 to 134 and employing the appropriate arylsulfonyl chloride and aminoguanidine derivative, the compounds shown in Table V are obtained and identified by HPLC and mass spectral analyses.

TABLE V

| EX NO | R2 | R5 | R6 | R10 | M + H | Time Min |
|---|---|---|---|---|---|---|
| 135 | H | H | H | phenyl | 382 | 4.48 |
| 136 | Br | H | H | phenyl | -0- | 4.80 |
| 137 | Cl | H | H | methyl | 354 | 4.54 |
| 138 | Cl | H | H | 4-methoxyphenyl | 446 | 4.59 |
| 139 | Cl | H | H | 2-naphthyl | 466 | 4.78 |
| 140 | Cl | H | H | 3,4-dimethoxyphenyl | 476 | 4.59 |
| 141 | H | —CH$_2$—CH$_2$— | | phenyl | — | — |
| 142 | Cl | —CH$_2$—CH$_2$— | | phenyl | — | — |

EXAMPLE 143

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10–25 μl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 μl. To each well is added the following mixture: 80.0 μl of incubation buffer made in 50 mM Tris.HCl buffer (pH 7.4) containing 10.0 mM $MgCl_2$ and 0.5 mM EDTA and 20 μl of [$^3$H]-LSD (S.A., 86.0 Ci/mmol, available from Amersham Life Science), 3.0 nM. The dissociation constant, $K_D$ of the [$^3$H]LSD at the human serotonin 5-HT6 receptor is 2.9 nM, as determined by saturation binding with increasing concentrations of [$^3$H]LSD. The reaction is initiated by the final addition of 100.0 μl of tissue suspension. Nonspecific binding is measured in the presence of 10.0 μM methiothepin. The test compounds are added in 20.0 μl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 μl Microscint®-20 scintillant to each shallow well. The unifilter plate is heat-sealed and counted in a PackardTop-Count® with a tritium efficiency of 31.0%.

Specific binding to the 5-HT6 receptor is defined as the total radioactivity bound less the amount bound in the presence of 10.0 μM unlabeled methiothepin. Binding in the presence of varying concentrations of test compound is expressed as a percentage of specific binding in the absence of test compound. The results are plotted as logit % bound versus log concentration of test compound. Nonlinear regression analysis of data points with a computer assisted program Prism® yields both the $IC_{50}$ and the $K_i$ values of test compounds with 95% confidence limits.

The amount of displacement by the test compound is given in percent (%) inhibition and is derived from the following equation:

$$\% \text{ inhibition} = \left(1 - \frac{B_0 - NSB}{TB - NSB}\right)100$$

where $B_0$ is the amount of CPM bound in the presence of the testing agent. NSB represents the CPM bound in the presence of a saturating concentration of a displacer and TB represents the total amount of CPM bound at zero (0) concentration of test compound.

Alternatively, a linear regression line of decline of data points is plotted, from which the $IC_{50}$ value can be read off and the $K_i$ value determined by solving the following equation:

$$K_i = \frac{IC_{50}}{1 + L/K_D}$$

where L is the concentration of the radioactive ligand used and $K_D$ is the dissociation constant of the ligand for the receptor, both expressed in nM. Using this assay, the % inhibition and $K_i$ values shown in Table VI are obtained.

TABLE VI

| Test Compound (Ex. No.) | Dose (nM) | % Inhibition | 5-HT6 Binding Ki (nM) |
|---|---|---|---|
| 1 | 1000 | 56.0 | — |
| 2 | 1000 | 69.2 | — |
| 3 | 1000 | 71.0 | — |
| 4 | 1000 | 71.9 | — |
| 5 | 1000 | 91.5 | — |
| 6 | 1000 | 97.8 | 11 |
| 7 | 1000 | 98.5 | 12 |
| 8 | 1000 | 95.2 | — |
| 9 | 1000 | 99.5 | 7 |
| 12 | 1000 | 75.6 | — |
| 13 | 1000 | 86.0 | — |
| 14 | 1000 | 85.4 | — |
| 15 | 100 | 67.1 | — |
| 16 | 10 | 40.6 | — |
| 17 | 10 | 52.0 | — |
| 18 | 100 | 77.9 | — |
| 19 | 100 | 82.4 | — |
| 20 | 100 | 76.3 | — |
| 21 | 1000 | 57.4 | — |
| 22 | 100 | 90.5 | 8 |
| 23 | 100 | 92.9 | 2 |
| 24 | 100 | 62.9 | — |
| 25 | 100 | 79.6 | 15 |
| 26 | 100 | 39.7 | — |
| 27 | 100 | 33.8 | — |
| 28 | 100 | 58.3 | — |
| 29 | 100 | 60.3 | — |
| 30 | 100 | 65.0 | — |
| 31 | 100 | 83.3 | 13 |
| 32 | 100 | 76.2 | 26 |
| 33 | 100 | 76.4 | 19 |
| 34 | 100 | 48.0 | — |
| 35 | 100 | 39.1 | — |
| 36 | 100 | 86.4 | 8 |
| 37 | 100 | 75.2 | 25 |
| 38 | 100 | 25.8 | — |
| 39 | 100 | 62.1 | — |
| 40 | 100 | 33.3 | — |
| 41 | 100 | 55.0 | — |
| 42 | 100 | 46.3 | — |
| 43 | 100 | 68.9 | — |
| 44 | 100 | 75.5 | 33 |
| 45 | 100 | 23.5 | — |
| 46 | 100 | 41.0 | — |
| 47 | 100 | 81.1 | 46 |
| 48 | 100 | 43.9 | — |
| 49 | 100 | 33.0 | — |
| 50 | 100 | 63.5 | — |
| 51 | 100 | 70.1 | — |
| 52 | 100 | 28.2 | — |
| 53 | 100 | 38.4 | — |
| 54 | 100 | 26.2 | — |
| 55 | 100 | 68.2 | — |
| 56 | 1000 | 76.9 | — |
| 57 | 100 | 40.4 | — |
| 58 | 100 | 78.3 | — |
| 59 | 1000 | 77.7 | — |
| 60 | 100 | 62.6 | — |
| 61 | 1000 | 83.6 | — |
| 62 | 1000 | 68.3 | — |
| 63 | 100 | 58.9 | — |
| 64 | 1000 | 89.6 | — |
| 65 | 1000 | 62.3 | — |
| 66 | 10 | 35.1 | — |
| 67 | 100 | 66.3 | — |
| 68 | 10 | 68.3 | — |
| 69 | 100 | 72.4 | 12 |
| 70 | 1000 | 89.8 | — |
| 71 | 100 | 61.5 | — |
| 72 | 100 | 75.1 | — |
| 73 | 1000 | 71.0 | — |
| 74 | 100 | 68.5 | — |
| 75 | 100 | 84.6 | — |
| 76 | 1000 | 74.5 | — |
| 77 | 10 | 44.3 | — |

TABLE VI-continued

| Test Compound (Ex. No.) | Dose (nM) | % Inhibition | 5-HT6 Binding Ki (nM) |
|---|---|---|---|
| 78 | 1000 | 85.5 | — |
| 79 | 1000 | 61.0 | — |
| 80 | 100 | 74.0 | — |
| 82 | 1000 | 46.9 | — |
| 83 | 1000 | 89.3 | — |
| 84 | 100 | 81.7 | — |
| 85 | 100 | 57.5 | — |
| 86 | 100 | 78.1 | — |
| 87 | 1000 | 88.9 | — |
| 88 | 1000 | 65.6 | — |
| 89 | 100 | 71.9 | — |
| 90 | 1000 | 63.5 | — |
| 91 | 1000 | 9.0 | — |
| 94 | 1000 | 27.9 | — |
| 95 | 1000 | 89.6 | — |
| 96 | 1000 | 20.0 | — |
| 98 | 1000 | 53.3 | — |
| 100 | 100 | 83.8 | 18 |
| 101 | 1000 | 77.4 | — |
| 102 | 10 | 41.1 | — |
| 103 | 100 | 69.4 | — |
| 104 | 1000 | 81.3 | — |
| 105 | 100 | 58.4 | — |
| 106 | 1000 | 64.4 | — |
| 107 | 1000 | 61.5 | — |
| 109 | 1000 | 67.8 | — |
| 110 | 1000 | 60.2 | — |
| 111 | 100 | 27.6 | — |
| 112 | 1000 | 94.6 | — |
| 114 | 100 | 85.2 | — |
| 115 | 1000 | 89.2 | — |
| 116 | 1000 | 73.5 | — |
| 117 | 100 | 78.2 | — |
| 118 | — | — | 7 |
| 119 | — | — | 2 |
| 120 | — | — | 85 |
| 121 | — | — | 9 |
| 122 | — | — | 101 |
| 123 | 100 | 34.0 | 12 |
| 124 | 100 | 75.2 | — |
| 125 | 100 | 39.1 | — |
| 126 | 100 | 37.7 | — |
| 127 | 100 | 83.3 | — |
| 128 | 100 | 23.9 | — |
| 129 | 100 | 23.4 | — |
| 130 | 100 | 49.6 | — |

What is claimed is:

1. A compound of formula I

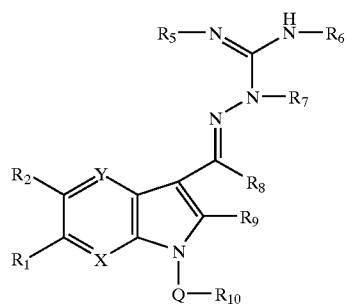

wherein
X is N or $CR_3$;
Y is N or $CR_4$;
Q is $SO_2$, CO, $CO_2$, $CONR$ or $CSNR_{12}$;
$R_1$, $R_2$, $R_3$ and $R_4$ are each independently H, halogen, CN, $OCO_2R_{13}$, $CO_2R_{14}$, $CONR_{15}R_{16}$, $NR_{17}SO_2R_{18}$, $NR_{19}COR_{28}$, $SO_nR_{20}$, $NR_{21}R_{22}$, $OR_{23}$, $COR_{24}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_5$, $R_6$ and $R_7$ are each independently H or a $C_1$–$C_6$alkyl, $C_2$–$C_6$alkenyl, $C_2$–$C_6$alkynyl, $C_3$–$C_{12}$cycloalkyl, cycloheteroalkyl, aryl or heteroaryl group each optionally substituted or $R_5$ and $R_6$ maybe taken together with the atoms to which they are attached to form an optionally substituted 5- to 7-membered ring;
$R_8$ is H or a $C_1$–$C_6$alkyl or $C_3$–$C_{10}$cycloalkyl group each optionally substituted;
$R_9$ is H, halogen, CN, $NO_2$, $NR_{25}R_{26}$, $OR_{27}$ or a $C_1$–$C_6$alkyl, aryl or heteroaryl group each optionally substituted or $R_8$ and $R_9$ may be taken together with the atoms to which they are attached to form an optionally substituted 5- to 7-membered ring optionally containing one or two heteroatoms selected from O, N or S;
$R_{10}$ is a $C_1$–$C_6$alkyl, aryl or heteroaryl group each optionally substituted or an optionally substituted 8- to 13-membered bicyclic or tricyclic ring system having a N atom at the bridgehead and optionally containing 1, 2 or 3 additional heteroatoms selected from N, O or S with the proviso that when $R_8$ is H or $C_1$–$C_6$alkyl and Q is CO then $R_{10}$ must be other than $C_1$–$C_6$alkyl or aryl;
n is 0 or an integer of 1 or 2;
$R_{11}$ and $R_{12}$ are each independently H or a $C_1$–$C_6$alkyl, aryl or heteroaryl group each optionally substituted;
$R_{13}$, $R_{14}$, $R_{18}$, $R_{20}$, $R_{23}$, $R_{24}$, $R_{27}$ and $R_{28}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_{15}$ and $R_{16}$ are each independently H or an optionally substituted $C_1$–$C_6$alkyl group; and
$R_{17}$, $R_{19}$, $R_{21}$, $R_{22}$, $R_{25}$ and $R_{26}$ are each independently H or an optionally substituted $C_1$–$C_4$alkyl group or $R_{21}$ and $R_{22}$ may be taken together with the atom to which they are attached to form a 5- to 7-membered ring optionally containing another heteroatom selected from O, N or S; or the stereoisomers thereof, the tautomers thereof or the pharmaceutically acceptable salts thereof.

2. The compound according to claim 1 wherein Q is $SO_2$.

3. The compound according to claim 1 wherein $R_{10}$ is an aryl or heteroaryl group each optionally substituted or an optionally substituted 8- to 13-membered bicyclic or tricyclic ring system having a N atom at the bridgehead and optionally containing 1, 2 or 3 additional heteroatoms selected from N, O or S.

4. The compound according to claim 1 wherein X is $CR_3$ and Y is $CR_4$.

5. The compound according to claim 2 wherein $R_9$ is H.

6. The compound according to claim 2 wherein X is $CR_3$; Y is $CR_4$; and $R_9$ is H.

7. The compound according to claim 6 wherein $R_{10}$ is an aryl or heteroaryl group each optionally substituted or an optionally substituted 8- to 13-member bicyclic or tricyclic ring system having a N atom at the bridgehead and optionally containing 1, 2 or 3 additional heteroatoms selected from N, O or S.

8. The compound according to claim 2 selected from the group consisting of:
2-[6-chloro-9-(phenylsulfonyl)-1,2,3,9-tetrahydro-4H-carbazol-4-ylidene]hydrazinecarboximidamide;
2-[6-chloro-9-(phenylsulfonyl)-1,2,3,9-tetrahydro-4H-carbazol-4-one 4,5-dihydro-1H-imidazol-2-ylhydrazone;

2-[6-chloro-9-(phenylsulfonyl)-1,2,3,9-tetrahydro-4H-carbazol-4-one 4,5-dihydro-1H-imidazol-2-yl(methyl)hydrazone;

2-[9-(phenylsulfonyl)-1,2,3,9-tetrahydro-4H-carbazol-4-ylidene]hydrazinecarboximidamide;

2-[6-bromo-9-(phenylsulfonyl)-1,2,3,9-tetrahydro-4H-carbazol-4-one 4,5-dihydro-1H-imidazol-2-ylhydrazone;

2-[6-bromo-9-(phenylsulfonyl)-1,2,3,9-tetrahydro-4H-carbazol-4-one 4,5-dihydro-1H-imidazol-2-yl(methyl)hydrazone;

2-[6-bromo-9-(phenylsulfonyl)-1,2,3,9-tetrahydro-4H-carbazol-4-ylidene]hydrazinecarboximidamide;

2-{6-chloro-9-[(4-methoxyphenyl)sulfonyl]-1,2,3,9-tetrahydro-4H-carbazol-4-ylidene}hydrazinecarboximidamide;

2-{9-[(2-amino-4-methyl-1,3-thiazol-5-yl)sulfonyl]-6-chloro-1,2,3,9-tetrahydro-4H-carbazol-4-ylidene}hydrazinecarboximidamide;

2-[6-chloro-9-(2-naphthylsulfonyl)-1,2,3,9-tetrahydro-4H-carbazol-4-ylidene]-hydrazinecarboximidamide;

2-{6-chloro-9-[(3,4-dimethoxyphenyl)sulfonyl]-1,2,3,9-tetrahydro-4H-carbazol-4-ylidene}hydrazinecarboximidamide;

2-(9-phenylsulfonyl-2,2,6-trimethyl-1,2,3,9-tetrahydro-4H-carbazol-4-ylidene)-hydrazinecarboximidamide;

2-(6-methyl-2-phenyl-9-phenylsulfonyl-1,2,3,9-tetrahydro-4H-carbazol-4-ylidene)hydrazinecarboximidamide;

2-(6-methyl-9-phenylsulfonyl-1,2,3,9-tetrahydro-4H-carbazol-4-ylidene)hydrazinecarboximidamide;

2-(6-isopropyl-2,2-dimethyl-9-phenylsulfonyl-1,2,3,9-tetrahydro-4H-carbazol-4-ylidene)hydrazinecarboximidamide;

2-(6-isopropyl-2-phenyl-9-phenylsulfonyl-1,2,3,9-tetrahydro-4H-carbazol-4-ylidene)hydrazinecarboximidamide;

2-[2,2-dimethyl-9-phenylsulfonyl-6-(trifluoromethoxy)-1,2,3,9-tetrahydro-4H-carbazol-4-ylidene]hydrazinecarboximidamide;

2-(6-bromo-2,2-dimethyl-9-phenylsulfonyl-1,2,3,9-tetrahydro-4H-carbazol-4-ylidene)-hydrazinecarboximidamide;

2-(6-bromo-2-phenyl-9-phenylsulfonyl-1,2,3,9-tetrahydro-4H-carbazol-4-ylidene)hydrazinecarboximidamide;

the stereoisomers thereof; and
the pharmaceutically acceptable salts thereof.

9. The compound according to claim 6 selected from the group consisting of:

1-[(4-methylphenyl)sulfonyl]-1H-indole-3-carboxaldehyde 1,4,5,6-tetrahydropyrimidin-2-ylhydrazone;

2-({1-[(4-methylphenyl)sulfonyl]-1H-indol-3-yl}methylidene)hydrazinecarboximidamide;

1-[(4-methylphenyl)sulfonyl]-1H-indole-3-carboxaldehyde 4,5-dihydro-1H-imidazol-2-yl(methyl)hydrazone;

2-{cyclohexyl[1-(phenylsulfonyl)-1H-indol-3-yl]methylidene}hydrazinecarboximidamide;

2-{2-methyl-1-[1-(phenylsulfonyl)-1H-indol-3-yl]propylidene}hydrazinecarboximidamide;

2-{2-phenyl-1-[1-(phenylsulfonyl)-1H-indol-3-yl]ethylidene}hydrazinecarboximidamide;

2-{3-methyl-1-[1-(phenylsulfonyl)-1H-indol-3-yl]butylidene}hydrazinecarboximidamide;

2-{1-[1-(phenylsulfonyl)-1H-indol-3-yl]ethylidene}hydrazinecarboximidamide;

2-{1-[5-chloro-2-methyl-1-(phenylsulfonyl)-1H-indol-3-yl]ethylidene}hydrazinecarboximidamide;

2-{1-[2-(4-fluorophenyl)-1-(phenylsulfonyl)-1H-indol-3-yl]ethylidene}hydrazinecarboximidamide;

2-{1-[5-cyano-1-(phenylsulfonyl)-1H-indol-3-yl]ethylidene}hydrazinecarboximidamide;

2-{1-[5-iodo-1-(phenylsulfonyl)-1H-indol-3-yl]ethylidene}hydrazinecarboximidamide;

2-{1-[5-nitro-1-(phenylsulfonyl)-1H-indol-3-yl]ethylidene}hydrazinecarboximidamide;

2-{1-[5-fluoro-1-(phenylsulfonyl)-1H-indol-3-yl]ethylidene}hydrazinecarboximidamide;

2-{[5-methoxy-1-(phenylsulfonyl)-1H-indol-3-yl]methylidene}hydrazinecarboximidamide;

2-{[5-(benzyloxy)-1-(phenylsulfonyl)-1H-indol-3-yl]methylidene}hydrazinecarboximidamide;

2-(1-{1-[(2-amino-4-methyl-1,3-thiazol-5-yl)sulfonyl]-1H-indol-3-yl}ethylidene)-hydrazinecarboximidamide;

2-(1-{1-[(4-aminophenyl)sulfonyl]-1H-indol-3-yl}ethylidene)hydrazinecarboximidamide;

2-{1-[1-(2,1,3-benzothiadiazol-4-ylsulfonyl)-1H-indol-3-yl]ethylidene}hydrazinecarboximidamide;

2-{1-[1-(2,1,3-benzoxadiazol-4-ylsulfonyl)-1H-indol-3-yl]ethylidene}hydrazinecarboximidamide;

2-{1-[1-([1,1'-biphenyl]-4-ylsulfonyl)-1H-indol-3-yl]ethylidene}hydrazinecarboximidamide;

2-(1-{1-[(4-bromo-2,5-dichlorothien-3-yl)sulfonyl]-1H-indol-3-yl}ethylidene)hydrazinecarboximidamide;

2-(1-{1-[(4-bromo-5-chlorothien-2-yl)sulfonyl]-1H-indol-3-yl}ethylidene)hydrazinecarboximidamide;

2-(1-{1-[(3-bromo-5-chlorothien-2-yl)sulfonyl]-1H-indol-3-yl}ethylidene)hydrazinecarboximidamide;

2-(1-{1-[(4-bromophenyl)sulfonyl]-1H-indol-3-yl}ethylidene)hydrazinecarboximidamide;

2-(1-{1-[(5-bromothien-2-yl)sulfonyl]-1H-indol-3-yl}ethylidene)hydrazinecarboximidamide;

2-(1-{1-[(5-chloro-2-methoxyphenyl)sulfonyl]-1H-indol-3-yl}ethylidene)hydrazinecarboximidamide;

2-(1-{1-[(5-chloro-3-methyl-1-benzothien-2-yl)sulfonyl]-1H-indol-3-yl}ethylidene)hydrazinecarboximidamide;

2-(1-{1-[(6-chloroimidazo[2,1-b][1,3]thiazol-5-yl)sulfonyl]-1H-indol-3-yl}ethylidene)hydrazinecarboximidamide;

2-(1-{1-[(5-chlorothien-2-yl)sulfonyl]-1H-indol-3-yl}ethylidene)hydrazinecarboximidamide;

2-[1-(1-{[5-(dimethylamino)-1-naphthyl]sulfonyl}-1H-indol-3-yl)ethylidene]hydrazinecarboximidamide;

2-(1-{1-[(4,5-dibromothien-2-yl)sulfonyl]-1H-indol-3-yl}ethylidene)hydrazinecarboximidamide;

2-(1-{1-[(2,5-dichlorophenyl)sulfonyl]-1H-indol-3-yl}ethylidene)hydrazinecarboximidamide;

2-(1-{1-[(2,5-dichlorothien-3-yl)sulfonyl]-1H-indol-3-yl}ethylidene)hydrazinecarboximidamide;

2-(1-{1-[(4,5-dichlorothien-2-yl)sulfonyl]-1H-indol-3-yl}ethylidene)hydrazinecarboximidamide;

2-(1-{1-[(3,5-dimethylisoxazol-4-yl)sulfonyl]-1H-indol-3-yl}ethylidene)hydrazinecarboximidamide;

2-(1-{1-[(4-fluorophenyl)sulfonyl]-1H-indol-3-yl}ethylidene)hydrazinecarboximidamide;
2-{1-[1-({5-[1-methyl-5-(trifluoromethyl)-1H-pyrazol-3-yl]thien-2-yl}sulfonyl]-1H-indol-3-yl]ethylidene}hydrazinecarboximidamide;
2-(1-{1-[(2-methyl-5-nitrophenyl)sulfonyl]-1H-indol-3-yl}ethylidene)hydrazinecarboximidamide;
2-(1-{1-[(1-methyl-1H-imidazol-4-yl)sulfonyl]-1H-indol-3-yl}ethylidene)hydrazinecarboximidamide;
2-[1-(1-{[4-(methylsulfonyl)phenyl]sulfonyl}-1H-indol-3-yl)ethylidene]hydrazinecarboximidamide;
2-{1-[1-({5-[2-(methylthio)pyrimidin-4-yl]thien-2-yl}sulfonyl)-1H-indol-3-yl]ethylidene}hydrazinecarboximidamide;
2-{1-[1-(1-naphthylsulfonyl)-1H-indol-3-yl]ethylidene}hydrazinecarboximidamide;
2-(1-{1-[(2-nitrophenyl)sulfonyl]-1H-indol-3-yl}ethylidene)hydrazinecarboximidamide;
2-(1-{1-[(4-nitrophenyl)sulfonyl]-1H-indol-3-yl}ethylidene)hydrazinecarboximidamide;
2-(1-{1-[(5-pyridin-2-ylthien-2-yl)sulfonyl]-1H-indol-3-yl}ethylidene)hydrazinecarboximidamide;
2-[1-(1-{[4-(trifluoromethoxy)phenyl]sulfonyl}-1H-indol-3-yl)ethylidene]hydrazinecarboximidamide;
2-(1-{1-[(4-methoxyphenyl)sulfonyl]-1H-indol-3-yl}ethylidene)hydrazinecarboximidamide;
2-(1-{1-[(4-methoxyphenyl)sulfonyl]-1H-indol-3-yl}pentylidene)hydrazinecarboximidamide;
2-(cyclopropyl{1-[(4-methoxyphenyl)sulfonyl]-1H-indol-3-yl}methylidene)hydrazinecarboximidamide;
2-{1-[1-(2-naphthylsulfonyl)-1H-indol-3-yl]ethylidene}hydrazinecarboximidamide;
2-{1-[1-(2-naphthylsulfonyl)-1H-indol-3-yl]pentylidene}hydrazinecarboximidamide;
2-{cyclopropyl[1-(2-naphthylsulfonyl)-1H-indol-3-yl]methylidene}hydrazinecarboximidamide;
2-{1-[1-(phenylsulfonyl)-1H-indol-3-yl]pentylidene}hydrazinecarboximidamide;
2-{cyclopropyl[1-(phenylsulfonyl)-1H-indol-3-yl]methylidene}hydrazinecarboximidamide;
2-(1-{1-[(3,4-dimethoxyphenyl)sulfonyl]-1H-indol-3-yl}ethylidene)hydrazinecarboximidamide;
2-(cyclopropyl{1-[(3,4-dimethoxyphenyl)sulfonyl]-1H-indol-3-yl}methylidene)hydrazine-carboximidamide;
2-(1-{5-chloro-1-[(4-methoxyphenyl)sulfonyl]-1H-indol-3-yl}ethylidene)-hydrazinecarboximidamide;
2-[{5-chloro-1-[(4-methoxyphenyl)sulfonyl]-1H-indol-3-yl}(cyclopropyl)methylidene]hydrazinecarboximidamide;
2-{1-[5-chloro-1-(2-naphthylsulfonyl)-1H-indol-3-yl]ethylidene}hydrazinecarboximidamide
2-{1-[5-chloro-1-(phenylsulfonyl)-1H-indol-3-yl]ethylidene}hydrazinecarboximidamide;
2-[[5-chloro-1-(phenylsulfonyl)-1H-indol-3-yl](cyclopropyl)methylidene]hydrazinecarboximidamide;
2-(1-{5-chloro-1-[(3,4-dimethoxyphenyl)sulfonyl]-1H-indol-3-yl}ethylidene)hydrazinecarboximidamide;
2-[{5-chloro-1-[(3,4-dimethoxyphenyl)sulfonyl]-1H-indol-3-yl}(cyclopropyl)-methylidene]hydrazincarboximidamide;
2-(cyclopropyl{6-fluoro-1-[(4-methoxyphenyl)sulfonyl]-1H-indol-3-yl}methylidene)-hydrazinecarboximidamide;
2-{1-[6-fluoro-1-(2-naphthylsulfonyl)-1H-indol-3-yl]ethylidene}hydrazinecarboximidamide;
2-{1-[6-fluoro-1-(phenylsulfonyl)-1H-indol-3-yl]ethylidene}hydrazinecarboximidamide;
2-{cyclopropyl[6-fluoro-1-(phenylsulfonyl)-1H-indol-3-yl]methylidene}hydrazinecarboximidamide;
2-(1-{1-[(3,4-dimethoxyphenyl)sulfonyl]-6-fluoro-1H-indol-3-yl}ethylidene)hydrazinecarboximidamide;
2-{1-[5-fluoro-1-(phenylsulfonyl)-1H-indol-3-yl]propylidene}hydrazinecarboximidamide;
2-(1-{1-[(4-aminophenyl)sulfonyl]-5-fluoro-1H-indol-3-yl}propylidene)hydrazinecarboximidamide;
2-{1-[5-fluoro-1-(2-naphthylsulfonyl)-1H-indol-3-yl]propylidene}hydrazinecarboximidamide;
2-(1-{1-[(4-aminophenyl)sulfonyl]-5-chloro-1H-indol-3-yl}propylidene)hydrazinecarboximidamide;
2-{1-[5-chloro-1-(2-naphthylsulfonyl)-1H-indol-3-yl]propylidene}hydrazinecarboximidamide;
N-(2-hydroxyethyl)-2-{1-[1-(phenylsulfonyl)-1H-indol-3-yl]ethylidene}hydrazinecarboximidamide the stereoisomers thereof; and
the pharmaceutically acceptable salts thereof.

10. A pharmaceutical composition which comprises a pharmaceutically acceptable carrier and an effective amount of a compound of formula I

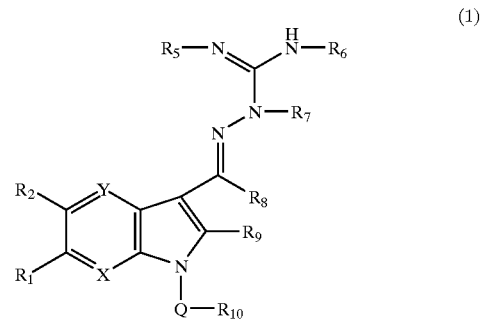

(1)

wherein
X is N or $CR_3$;
Y is N or $CR_4$;
Q is $SO_2$, CO, $CO_2$, CONR or $CSNR_{12}$;
$R_1$, $R_2$, $R_3$ and $R_4$ are each independently H, halogen, CN, $OCO_2R_{13}$, $CO_2R_{14}$, $CONR_{15}R_{16}$, $NR_{17}SO_2R_{18}$, $NR_{19}COR_{28}$, $SO_nR_{20}$, $NR_{21}R_{22}$, $OR_{23}$, $COR_{24}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_5$, $R_6$ and $R_7$ are each independently H or a $C_1$–$C_6$alkyl, $C_2$–$C_6$alkenyl, $C_2$–$C_6$alkynyl, $C_3$–$C_{12}$cycloalkyl, cycloheteroalkyl, aryl or heteroaryl group each optionally substituted or $R_5$ and $R_6$ maybe taken together with the atoms to which they are attached to form an optionally substituted 5- to 7-membered ring;
$R_8$ is H or a $C_1$–$C_6$alkyl or $C_3$–$C_{10}$cycloalkyl group each optionally substituted;
$R_9$ is H, halogen, CN, $NO_2$, $NR_{25}R_{26}$, $OR_{27}$ or a $C_1$–$C_6$alkyl, aryl or heteroaryl group each optionally substituted or $R_8$ and $R_9$ may be taken together with the atoms to which they are attached to form an optionally substituted 5- to 7-membered ring optionally containing one or two heteroatoms selected from O, N or S;

$R_{10}$ is a $C_1$–$C_6$alkyl, aryl or heteroaryl group each optionally substituted or an optionally substituted 8- to 13-membered bicyclic or tricyclic ring system having a N atom at the bridgehead and optionally containing 1, 2 or 3 additional heteroatoms selected from N, O or S with the proviso that when $R_8$ is H or $C_1$–$C_6$alkyl and Q is CO then $R_{10}$ must be other than $C_1$–$C_6$alkyl or aryl;

n is 0 or an integer of 1 or 2;

$R_{11}$ and $R_{12}$ are each independently H or a $C_1$–$C_6$alkyl, aryl or heteroaryl group each optionally substituted;

$R_{13}$, $R_{14}$, $R_{18}$, $R_{20}$, $R_{23}$, $R_{24}$, $R_{27}$ and $R_{28}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{15}$ and $R_{16}$ are each independently H or an optionally substituted $C_1$–$C_6$alkyl group; and $R_{17}$, $R_{19}$, $R_{21}$, $R_{22}$, $R_{25}$ and $R_{26}$ are each independently H or an optionally substituted $C_1$–$C_4$alkyl group or $R_{21}$ and $R_{22}$ may be taken together with the atom to which they are attached to form a 5- to 7-membered ring optionally containing another heteroatom selected from O, N or S; or the stereoisomers thereof, the tautomers thereof or the pharmaceutically acceptable salts thereof.

11. The composition according to claim 10 having a formula I compound wherein Q is $SO_2$.

12. The composition according to claim 11 having a formula I compound wherein $R_{10}$ is an aryl or heteroaryl group each optionally substituted or an optionally substituted 8- to 13-member bicyclic or tricyclic ring system having a N atom at the bridgehead and optionally containing 1, 2 or 3 additional heteroatoms selected from O, N or S.

13. The composition according to claim 1 having a formula I compound wherein X is $CR_3$ and Y is $CR_4$.

14. The composition according to claim 13 having a formula I compound wherein $R_9$ is H.

* * * * *